US009642912B2

(12) United States Patent
Kisak et al.

(10) Patent No.: US 9,642,912 B2
(45) Date of Patent: *May 9, 2017

(54) TOPICAL FORMULATIONS FOR TREATING SKIN CONDITIONS

(71) Applicant: Crescita Therapeutics Inc., Mississauga (CA)

(72) Inventors: Edward T. Kisak, San Diego, CA (US); John M. Newsam, La Jolla, CA (US); Dominic King-Smith, San Diego, CA (US); Pankaj Karande, Troy, NY (US); Samir Mitragotri, Santa Barbara, CA (US); Wade A. Hull, Kaysville, UT (US); Ngoc Truc-Chi Vo, Longueuil (CA)

(73) Assignee: Crescita Therapeutics Inc., Mississauga (CA)

( * ) Notice: Subject to any disclaimer, the term of this patent is extended or adjusted under 35 U.S.C. 154(b) by 204 days.

This patent is subject to a terminal disclaimer.

(21) Appl. No.: 14/578,812

(22) Filed: Dec. 22, 2014

(65) Prior Publication Data
US 2015/0297723 A1 Oct. 22, 2015

Related U.S. Application Data

(63) Continuation-in-part of application No. 13/791,460, filed on Mar. 8, 2013, now Pat. No. 9,308,181, which is a continuation-in-part of application No. 13/680,623, filed on Nov. 19, 2012, now Pat. No. 8,513,304, which is a continuation of application No. 12/848,792, filed on Aug. 2, 2010, now Pat. No. 8,343,962, which is a continuation-in-part of application No. 12/281,561, filed as application No. PCT/IB2007/001983 on Mar. 6, 2007, now Pat. No. 7,795,309.

(60) Provisional application No. 60/778,847, filed on Mar. 6, 2006.

(51) Int. Cl.
A61K 31/56 (2006.01)
A61K 47/18 (2017.01)
A61K 31/573 (2006.01)
A61K 47/14 (2017.01)
A61K 47/12 (2006.01)
A61K 9/00 (2006.01)
A61K 47/20 (2006.01)
A61K 9/06 (2006.01)
A61F 7/03 (2006.01)
A61F 7/02 (2006.01)

(52) U.S. Cl.
CPC ............ *A61K 47/183* (2013.01); *A61F 7/03* (2013.01); *A61K 9/0014* (2013.01); *A61K 9/06* (2013.01); *A61K 31/573* (2013.01); *A61K 47/12* (2013.01); *A61K 47/14* (2013.01); *A61K 47/20* (2013.01); *A61F 2007/0261* (2013.01)

(58) Field of Classification Search
CPC ..................................................... A61K 31/57
USPC ........................................................ 514/171
See application file for complete search history.

(56) References Cited

U.S. PATENT DOCUMENTS

| | | |
|---|---|---|
| 5,602,183 A | 2/1997 | Martin et al. |
| 5,648,380 A | 7/1997 | Martin |
| 5,874,479 A | 2/1999 | Martin |
| 6,328,979 B1 | 12/2001 | Yamashita et al. |
| 7,001,592 B1 | 2/2006 | Traynor et al. |
| 7,795,309 B2 | 9/2010 | Kisak et al. |
| 8,343,962 B2 | 1/2013 | Kisak et al. |
| 8,513,304 B2 | 8/2013 | Kisak et al. |
| 8,535,692 B2 | 9/2013 | Pongpeerapat et al. |
| 9,308,181 B2 * | 4/2016 | Kisak ............... A61K 47/12 |
| 2002/0006435 A1 | 1/2002 | Samuels et al. |
| 2002/0064524 A1 | 5/2002 | Cevc |
| 2005/0014823 A1 | 1/2005 | Soderlund et al. |
| 2005/0075407 A1 | 4/2005 | Tamarkin et al. |
| 2005/0196354 A1 | 9/2005 | Soshinsky |
| 2006/0229364 A1 | 10/2006 | Hobbs et al. |
| 2008/0075793 A1 | 3/2008 | Dunshee et al. |
| 2011/0028460 A1 | 2/2011 | Kisak et al. |
| 2013/0079371 A1 | 3/2013 | Sundberg et al. |
| 2013/0079404 A1 | 3/2013 | Kisak et al. |
| 2013/0165504 A1 | 6/2013 | Bancel et al. |
| 2013/0259924 A1 | 10/2013 | Bancel et al. |

FOREIGN PATENT DOCUMENTS

| | | |
|---|---|---|
| GB | 2008946 | 6/1979 |
| WO | WO 96/33706 | 10/1996 |
| WO | WO 2005/009510 | 2/2005 |

(Continued)

OTHER PUBLICATIONS

PCT Application No. PCT/CA2014/051049: Filing date Oct. 31, 2014; Nuvo Research Inc.; International Search Report mailed Feb. 10, 2015.

(Continued)

*Primary Examiner* — Raymond Henley, III
(74) *Attorney, Agent, or Firm* — Thorpe North & Western, LLP

(57) ABSTRACT

The present disclosure is drawn to topical formulations and related methods. In one embodiment, a topical formulation is provided that includes at least one corticosteroid, a first compound, and a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

46 Claims, 4 Drawing Sheets

(56) References Cited

FOREIGN PATENT DOCUMENTS

WO  WO 2005/018530  3/2005
WO  WO 2013/106496  7/2013

OTHER PUBLICATIONS

Teixeira, et al.; "Local anesthetic-induced microscopic and mesoscopic effects in micelles. A fluorescence, spin label and SAXS"; 2001Biochimica et Biophysica; ACTA 1510 (2001) pp. 93-105.

* cited by examiner

TOPICAL FORMULATIONS FOR TREATING SKIN CONDITIONS

This application is a continuation-in-part of U.S. patent application Ser. No. 13/791,460 filed on Mar. 8, 2013 and issued as U.S. Patent No. 9,308,181, which is a continuation-in-part of U.S. patent application Ser. No. 13/680,623, filed Nov. 19, 2012 and issued as U.S. Pat. No. 8,513,304, which was a continuation of U.S. patent application Ser. No. 12/848,792, filed Aug. 2, 2010 and issued as U.S. Pat. No. 8,343,962, which was a continuation-in-part of U.S. patent application Ser. No. 12/281,561, filed on Jan. 12, 2009 and issued as U.S. Pat. No. 7,795,309, which was a national stage of PCT/IB2007/001983 filed on Mar. 6, 2007, which claimed priority to U.S. Provisional Application Ser. No. 60/788,847, each of which is incorporated herein by reference.

BACKGROUND

Topical formulations for application to the skin can be useful in cosmetic applications, for treating conditions of the upper skin layers, and for transdermal administration of active agents to the local tissue underlying the skin or into the blood for systemic distribution. For example, using a topical formulation of a pharmaceutical agent is advantageous because it can avoid first-pass metabolism, circumvent gastrointestinal ("GI") absorption, allow delivery of an active ingredient with a relatively short biological half-life and/or a narrow therapeutic window, and facilitate uniform plasma dosing of the active ingredient, and/or can improve user compliance.

In spite of the advantages, transdermal administration is usually limited to about a dozen small lipophilic drugs, available in transdermal patch format (including scopolamine, fentanyl, estradiol, nitroglycerine, nicotine, and testosterone). Skin has evolved to impede the flux of exogenous molecules so as to provide a strong barrier to molecular delivery, particularly agents such as pharmaceutical agents. Transdermal drug administration is difficult because skin is an excellent diffusion barrier.

Structurally, the skin consists of two principal parts: (i) a relatively thin outermost layer (the "epidermis"), and (ii) a thicker inner region (the "dermis"). The outermost layer of the epidermis (the "stratum corneum") consists of flattened dead cells which are filled with keratin. The region between the flattened dead cells of the stratum corneum is filled with lipids which form lamellar phases. The highly impermeable nature of skin is due primarily to the stratum corneum. The viable epidermis underlying the stratum corneum is akin to other living tissue. The dermis provides the skin's structural strength as well as the nerve and vascular networks that support the epidermis.

Delivering an active agent into or through the skin in sufficient concentrations often utilizes some means for reducing the stratum corneum's hindrance of penetration. A number of methods for lowering the stratum corneum's barrier properties have been developed, including electrically assisted techniques such as iontophoresis or ultrasound, and bypassing the stratum corneum through microneedle arrays or ablation.

Molecular or chemical penetration enhancers provide an effective and inexpensive means of temporarily reducing skin resistance to the administration and passage of actives and other molecules. Molecular penetration enhancers or MPE™s can enhance the application to and/or diffusion of molecules across the skin by, for example, disrupting the lipid bilayers of the stratum corneum.

Over 300 substances have been identified as MPE™s but surprisingly few have been successfully developed into commercial formulations. Many potent MPE™s are irritating to the cells of the epidermis which can limit both the choice and concentration of MPE™s suitable for topical formulations. Discovery of new MPE™s to increase skin permeability is a highly desirable area and has had high activity over the last 30 years. However, the number of substances identified to be penetration enhancers is still relatively small when considering the more than 25,000,000 substances identified in the CAS registry (Chemical Abstracts Service, Columbus, Ohio, www.cas.org). The number of candidate drugs suitable for topical and transdermal administration could be significantly increased with improved penetration enhancers.

SUMMARY

With this background in mind, the present disclosure is drawn to topical formulationstransdermal systems, and methods for treating skin conditions. In one embodiment, a topical formulation is provided that comprises (i) at least one corticosteroid, (ii) a first compound, and (iii) a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

In another embodiment, a method of treating a skin condition such as psoriasis or dermatitis can comprise topical or transdermal administration of a corticosteroid to a subject. The formulation can comprise at least one corticosteroid, a first compound, and a second compound. The first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate. In one embodiment, the first and second compound can improve the flux and/or stability of the topical formulation when compared to a comparative formulation devoid of the first compound and the second compound and replaced with an equivalent wt % of water. In another embodiment, the first and second compound can improve the flux of the at least one corticosteroid into the skin surface when compared to a comparative formulation devoid of the first compound and the second compound and replaced with an equivalent wt % of water. In a further embodiment, the first and second compound can improve the stability of the topical formulation when compared to a comparative formulation devoid of the first compound and the second compound and replaced with an equivalent wt % of water. For example, the first and second compound can improve the amount of active degradation, change in viscosity and/or change in pH over a period of time.

BRIEF DESCRIPTION OF THE DRAWINGS

Reference will now be made to the exemplary embodiments illustrated, and specific language will be used herein to describe the same. It will nevertheless be understood that no limitation of the scope of the invention is thereby intended.

DETAILED DESCRIPTION

Figure 1:
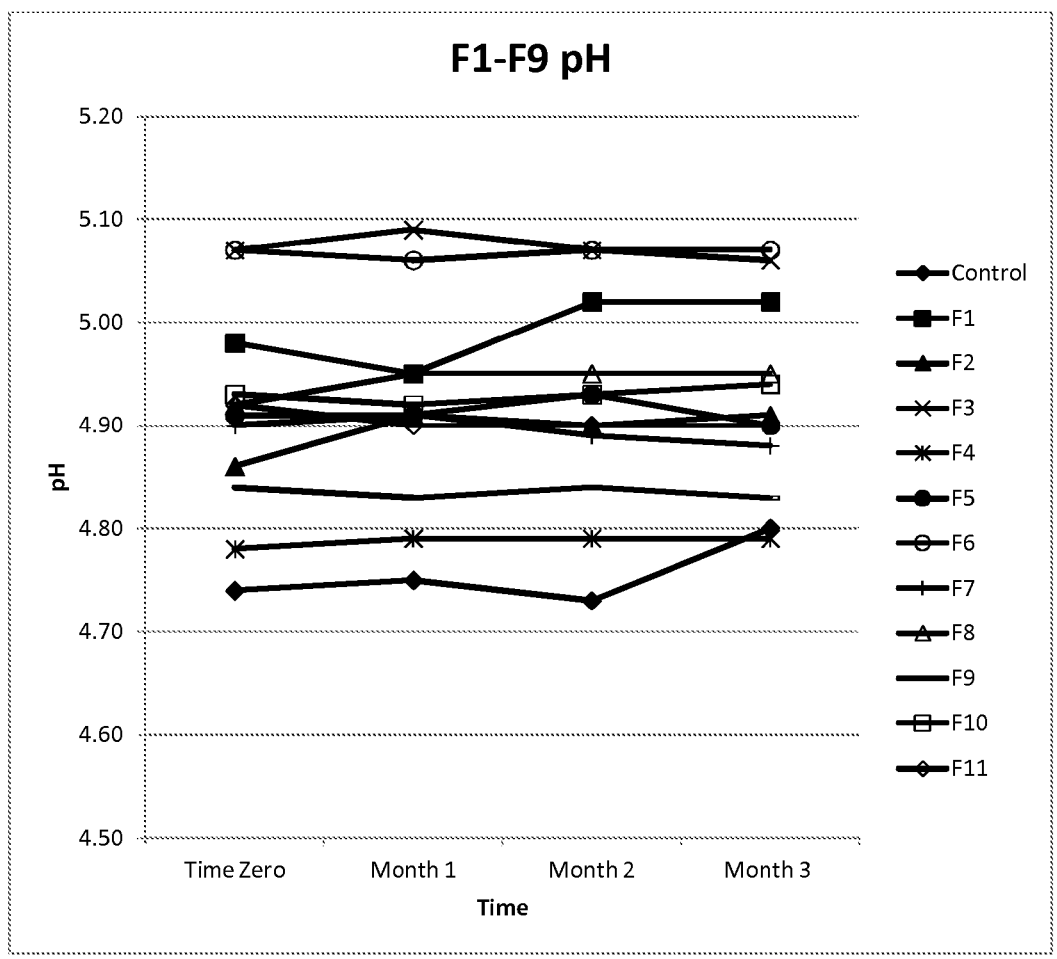
FIG. 1 is a plot of the pH of several exemplary embodiments of formulations disclosed herein.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a corticosteroid" includes reference to one or more of such corticosteroids.

As used herein, the term "active agent" indicates a compound or mixture of compounds, that when added to a composition, tend to produce a particular therapeutic effect.

As used herein, the term "comparative formulation" is a formulation that is compositionally identical with the exception that amounts (wt %) of the first compound and second compound are each replaced with the same amount (wt %) of water.

"Multiplexed molecular penetration enhancers" ("MMPE™") as described herein include N-lauroyl sarcosine, sodium octyl sulfate, methyl laurate, isopropyl myristate, oleic acid, glyceryl oleate, and sodium lauryl sulfoacetate, and in accordance with examples described herein, typically they are used in combination, e.g., two or more. The use of a permeation enchancer(s) can be incorporated in a topical formulation to facilitate administration of one or more active ingredients. The increased penetration enhancement can also lead to a reduction in the amount of skin irritants in a formulation.

The term "penetration enhancer" is used herein to refer to an agent that improves the transport of molecules such as an active agent (e.g., a medicine) into or through the skin. Various conditions may occur at different sites in the body either in the skin or below creating a need to target delivery of compounds. For example, a psoriasis treatment may benefit from delivery of therapeutic drug levels in the deeper tissue. A "penetration enhancer" may be used to assist in the delivery of an active agent directly to the skin or underlying tissue or indirectly to the site of the disease through systemic distribution. A penetration enhancer may be a pure substance or may comprise a mixture of different chemical entities. In this specification the terms "penetration enhancer," "chemical penetration enhancer," "multiplexed molecular penetration enhancer," and "MMPE™" can be used interchangeably.

"Skin" is defined to include human skin (intact, diseased, ulcerous, or broken) as well as mucosal surfaces that are usually at least partially exposed to air such as lips, genital and anal mucosa, and nasal and oral mucosa.

As used herein, the term "skin contact region" refers to an area wherein the topical formulation contacts the skin.

The term "subject" as used herein includes all members of the animal kingdom, including mammals, and most typically, refers to humans.

The term "topical administration" is used in its conventional sense to mean delivery of a substance, such as a therapeutically active agent, into the skin or a localized region of the body. Topical administration of a drug may often be advantageously applied in, for example, the treatment of various skin disorders or conditions.

As used herein the term "topical formulation" refers to a formulation that may be applied to skin or a mucosa. Topical formulations may, for example, be used to confer therapeutic benefit to a patient or cosmetic benefits to a consumer. Topical formulations can be used for both topical and transdermal administration of substances.

As used herein, the term "transdermal" means in the broadest sense into or through the skin. Further the terms "transdermal" and "percutaneous" are used interchangeably throughout this specification.

The term "transdermal administration" is used to mean administration through the skin. Transdermal administration is often applied where systemic delivery of an active is desired, although it may also be useful for delivering an active to tissues underlying the skin with minimal systemic absorption (i.e. localized delivery).

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

The term "water" as an ingredient in the compositions of the compositions of the present disclosure refers to pharmaceutically-acceptable water.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about ±10% of the numerical value. In another embodiment, the degree of flexibility can be within about ±5% of the numerical value. In a further embodiment, the degree of flexibility can be within about ±2%, ±1%, or ±0.05%, of the numerical value.

As used herein, a plurality of active agents and/or compounds may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 mm to 2.0 mm" should be interpreted to include not only the explicitly recited values of about 0.01 mm to about 2.0 mm, but also include individual values and sub-ranges within the indicated range. Thus, included in this numerical range are individual values such as 0.5 mm, 0.7 mm, and 1.5 mm, and sub-ranges such as from 0.5 mm to 1.7 mm, 0.7 mm to 1.5 mm, and from 1.0 mm to 1.5 mm, etc. Furthermore, such an interpretation should apply regardless of the breadth of the range or the characteristics being described. Additionally, it is noted that all percentages are in weight, unless specified otherwise.

The present disclosure is drawn to various formulations and methods in the area of topical and transdermal delivery. MMPE™s can be used to improve the administration and increase penetration of active agents, such as corticosteroids into and through the skin. These compounds can thus act as excellent penetration enhances, particularly when used in combination—i.e. two (or more) compounds are selected from N-lauroyl sarcosine, sodium octyl sulfate, methyl laurate, isopropyl myristate, oleic acid, glyceryl oleate, or sodium lauryl sulfoacetate.

Examples of combinations of compounds that can act to improve penetration include the following:

the first compound comprises methyl laurate and the second comprises isopropyl myristate;

the first compound comprises methyl laurate and the second comprises oleic acid; the first compound comprises methyl laurate and the second comprises glyceryl oleate;

the first compound comprises methyl laurate and the second comprises sodium lauryl sulfoacetate;

the first compound comprises isopropyl myristate and the second compound comprises oleic acid;

the first compound comprises isopropyl myristate and the second compound comprises glycerol oleate;

the first compound comprises isopropyl myristate and the second compound comprises sodium lauryl sulfoacetate;

the first compound comprises oleic acid and the second compound comprises glycerol oleate;

the first compound comprises oleic acid and the second compound comprises sodium lauryl sulfoacetate; and the first compound comprises glycerol oleate and the second compound comprises sodium lauryl sulfoacetate.

The first and second compounds can be present in the topical formulation at a weight ratio of first compound to second compound of about 1:9 to about 9:1. In another embodiment, the first and second compounds can be present in the topical formulation at a weight ratio of first compound to second compound of about 1:5 to about 5:1, about 1:4 to about 4:1, about 1:3 to about 3:1, about 1:2 and about 2:1, and about 1:1.

The first and second compound can collectively be present in the composition in amounts up to about 50 wt %, e.g., 0.1 wt % to 50 wt %. More typically, the total concentration of the first compound and the second compound is up to about 40 wt %, e.g., 0.1 wt % to 40 wt %. In another example, the total concentration of the first compound and the second compound is in the range of from about 1 wt % to about 35 wt %. Even more typically, the total concentration of the first compound and the second compound is in the range of from about 1 wt % to about 30 wt %. Even more typically, the total concentration of the first compound and the second compound is in the range of from about 1 wt % to about 25 wt %. Even more typically, the total concentration of the first compound and the second compound is in the range of from about 1 wt % to about 20 wt %. Even more typically, the total concentration of the first compound and the second compound is in the range of from about 1 wt % to about 15 wt %. Even more typically, the total concentration of the first compound and the second compound is in the range of from about 1 wt % to about 10 wt % per unit volume of the formulation. Even more typically, the total concentration of the first compound and the second compound is in the range of from about 1 wt % to about 7.5 wt %. In still another example, the total concentration of the first compound and the second compound are in the range of from about 1 wt % to about 5 wt % per unit volume of the formulation. Within these ranges, it can in some cases, be desirable to have the total concentration of the first compound and the second compound in the range of from about 1.5 wt % to about 3 wt % per unit volume of the formulation.

In one aspect of the present disclosure, as mentioned, the at least one active agent is a corticosteroid. Generally, any corticosteroid known in the art can be incorporated into topical formulations and systems disclosed herein. Non-limiting examples of such corticosteroids include alclometasone dipropionate, amcinonide, beclomethasone dipropionate, betamethasone, betamethasone benzoate, betamethasone dipropionate, betamethasone valerate, budesonide, clobetasol propionate, desonide, desoximetasone, dexamethasone, diflorasone diacetate, fludrocortisone acetate, flunisolide, flurandrenolide, fluocinolone acetonide, fluocinonide, fluticasone propionate, halcinonide, halobetasol, halobetasol propionate, hydrocortisone, hydrocortisone valerate, methylprednisolone, mometasone furoate, prednisolone, prednisone, triamcinolone, triamcinolone acetonide, or combinations thereof in another embodiment, the topical formulations comprises a corticosteroid and one or more additional agents selected from retinoids (e.g. tretinoin, adapalene, tazarotene, among others), Vitamin D and Vitamin analogs, JAK inhibitors, kinase inhibitors, phosphodiesterase inhibitors, coal tar and coal tar extracts, keratolytics and combinations thereof.

The corticosteroid can be present in the formulation up to about 20 wt %, e.g., 0.01 wt % to about 20 wt %, typically from about 0.05 wt % to about 10 wt %, and more typically from about 0.05 wt % to about 5 wt %. In one embodiment, the corticosteroid can be a pharmaceutically acceptable salt of a corticosteroid. In a further embodiment, the corticosteroid can be a pharmaceutically acceptable base of a corticosteroid. In one embodiment, the corticosteroid can include clobetasol, halobetasol, betamethasone, triamcinolone acetonide and derivatives and combinations thereof. Most preferably the corticosteroid is halobetasol propionate, see Formula I below.

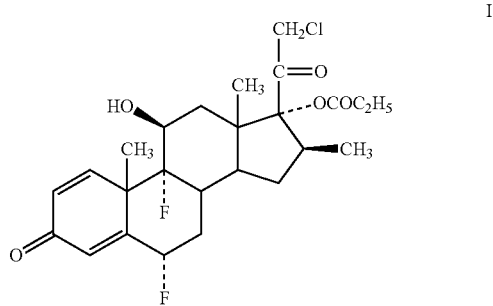

In one embodiment, halobetasol propionate is used to treat a variety of skin conditions including but not limited to psoriasis, eczema, dermatitis, allergies, and skin rashes. In a preferred embodiment, the halobetasol propionate formulation is used to treat psoriasis. In yet another embodiment, the halobetasol propionate formulation is used to treat moderate to severe plaque psoriasis and is delivered into the superficial layers of the skin.

In one embodiment, the formulation comprises 0.05% w/w halobetasol propionate, 0.5% w/w methyl laurate, and 1% w/w isopropyl myristate, along with various solvents, emollients/surfactants, and preservatives. In another embodiment, the formulation comprises 0.05% w/w halobetasol propionate, 0.5% w/w methyl laurate, and 1% w/w oleic acid along with various solvents, emollients/surfactants, and preservatives. In yet another embodiment, the formulation comprises 0.05% w/w halobetasol propionate, 0.5% w/w methyl laurate, and 1% w/w glyceryl oleate, along with various solvents, emollients/surfactants, and preservatives. In a further embodiment, the formulation comprises 0.05% w/w halobetasol propionate, 0.5% w/w methyl laurate, and 1% w/w sodium lauryl sulfoacetate, along with various solvents, emollients/surfactants, and preservatives. In another embodiment, the formulation comprises 0.05% w/w halobetasol propionate, 1% w/w isopropyl myristate, and 1% w/w oleic acid, along with various solvents, emollients/surfactants, and preservatives. In yet another embodiment, the formulation comprises 0.05% w/w halobetasol propionate, 1% w/w isopropyl myristate, and 1% w/w glyceryl oleate, along with various solvents, emollients/surfactants, and preservatives. In a further embodiment, the formulation comprises 0.05% w/w halobetasol propionate, 1% w/w isopropyl myristate, and 1% w/w sodium lauryl sulfoacetate, along with various solvents, emollients/surfactants, and preservatives. In another embodiment, the formulation comprises 0.05% w/w halobetasol propionate, 1% w/w oleic acid, and 1% w/w glyceryl oleate, along with various solvents, emollients/surfactants, and preservatives. In yet another embodiment, the formulation comprises 0.05% w/w halobetasol propionate, 1% w/w oleic acid, and 1% w/w sodium lauryl sulfoacetate, along with various solvents, emollients/surfactants, and preservatives. In a further embodiment, the formulation comprises 0.05% w/w halobetasol propionate, 1% w/w glyceryl oleate, and 1% w/w sodium lauryl sulfoacetate, along with various solvents, emollients/surfactants, and preservatives.

The combination of at least two MMPE™s in a corticosteroid containing formulation is shown herein to enhance stability and/or penetration of the corticosteroid through the skin. More specifically, the compounds act as excellent penetration enhancers and are shown to have an amplified effect when used in a combination, i.e. two (or more) MMPE™ compounds wherein the first compound and second compound are each selected from the group of N-lauroyl sarcosine, sodium octyl sulfate, methyl laurate, isopropyl myristate, oleic acid, glyceryl oleate, and sodium lauryl sulfoacetate. Again and in further detail, examples of combinations of first and second compounds that act as improved penetration enhancers can include: isopropyl myristate and sodium lauryl sulfoacetate; oleic acid and sodium lauryl sulfoacetate; glyceryl oleate and sodium lauryl sulfoacetate; and methyl laurate and sodium lauryl sulfoacetate; to name a few.

The formulation can have increased penetration of the corticosteroid through the skin when compared to a comparative formulation devoid of the MMPE™s (with an equivalent wt % of water replacing the MMPE™s). The increase in penetration of the corticosteroid can be at least 5%, at least 10%, at least 20%, at least 30%, at least 40%, at least 50%, at least 60%, at least 70%, at least 80%, at least 90%, at least 100%, at least 250%, at least 500%, at least 750%, at least 1,000%, at least 2,000%, at least 3,000%, at least 4000% or even at least 8,000% greater than the penetration of the comparative formulation at a given period of time during the application. Over the course of a thirty hour application period, the increase in penetration of the corticosteroid can be at least 800% greater, at least 900% greater, at least 1,000% greater, at least 1,250% greater, or even at least 1,500% greater when compared to the comparative formulation. This increased penetration enhancement can also lead to a reduction in the total concentration of potential skin irritants in a formulation. It has been found that the presence of the MMPE™s do not negatively affect the stability of the active ingredient in the formulation or the physical stability of the formulation.

Alternatively, or in addition to the ability to improve the penetration of the corticosteroid through the skin when compared to a comparative formulation devoid of the MMPE™s (with an equivalent wt % of water replacing the MMPE™s), the first and second compounds present in the topical formulations may function to improve the stability of the formulation.

Long storage periods can result in increased active degradation, changes in pH and changes in viscosity. One of the benefits of the topical formulations disclosed herein is the improved physical and/or chemical stability of the formulations when stored. In one embodiment, the formulation comprising a first compound and a second compound may have an enhanced physical stability. For example, in one aspect, the topical formulation can have improved consistency of viscosity after being stored for 12 weeks, 6 months, 12 months or 24 months at 25° C. compared to a comparative formulation devoid of the first compound and the second compound (where the first and second compounds are replaced with a commensurate amount of water, i.e. equal weight percentage of water to replace the removed first and second compounds). In still another embodiment, the topical formulation can have a viscosity that is at least 50% more, at least 25% more, or at least 10% more consistent with the formulation's initial viscosity after 12 weeks, 6 months, 12 months or 24 months when stored at about 25° C. compared to a comparative formulation devoid of the first compound and the second compound (again as in each of these examples, replacing the removed first and second compounds with an equivalent amount of water).

In addition to the improvements in physical stability, the topical formulations of the present invention may have improvements in chemical stability, for example, decreased active degradation and/or improved pH stability. In one embodiment, the topical formulations disclosed herein can provide improved chemical stability after being stored for a period of 12 weeks, 6 months, 12 months or 24 months at 25° C. such that the formulation has less degradation of the active ingredient as compared to a comparative formulation devoid of the first and second compound (again with an equivalent amount of water added thereto to replace the first and second compounds). In another embodiment, the topical formulations disclosed herein can provide improved pH stability after being stored for 12 weeks, 6 months, 12 months or 24 months at 25° C. compared to a comparative formulation devoid of the first compound and the second compound (again with an equivalent amount of water added thereto to replace the first and second compounds). For example, the topical formulation can have a pH that is at least 50% more, at least 25% more, or at least 10% more consistent with the formulation's initial pH after 12 weeks, 6 months, 12 months or 24 months when stored at about 25° C. compared to a comparative formulation devoid of the first compound and the second compound stored under the same conditions for the same amount of time.

Improved physical and/or chemical stability of topical formulations may lead to increased commercial shelf life of the system. In one embodiment, the topical formulation of the invention can have an increased shelf life of about 3 months, about 6 months, about 9 months or about 12 months compared to a comparative formulation devoid of the first compound and the second compound stored under the same conditions. In another embodiment the shelf life of the topical formulation can be at least about 27-months, at least about 30 months, at least about 33 months, or at least about 36 months.

The topical formulations of the present disclosure may also be formulated to include other chemical penetration enhancers which have significant ability to enhance transport of the corticosteroid and/or other active agents present in the topical formulations. Such substances may have the character of surfactants, azone-like compounds, solvents, alcohols, fatty acids, fatty esters, aliphatic thiols, and the like. Examples of chemical penetration enhancers are reported in the paper of Santus et al. (Santus, C. G. and Baker, R. W., Transdermal enhancer patent literature. Journal of Controlled Release 1993.25:1-20.) The penetration enhancing effect may be measured using techniques known in the art. An example of one measurement method is described in the Examples below.

The topical formulations can also include other components as well. Examples of additional compounds that can be included in the topical formulations include water, thickening, gelling and/or solidifying polymers, emollients/surfactants excipients, fatty acid esters, parabens, solvents, and/or the like. In one embodiment, the topical formulation can include water, and in some case, the water can be the ingredient that is present at the single greatest concentration.

Other suitable carriers or excipients that may be used in the topical formulations discussed herein are known in the art and include, but are not limited to, solubilizers such as $C_2$ to $C_8$ straight and branched chain alcohols, diols and triols, moisturizers and humectants such as glycerine, amino acids and amino acid derivatives, polyaminoacids and derivatives, pyrrolidone carboxylic acids and their salts and derivatives, surfactants such as sodium laureth sulfate, sorbitan monolaurate, emulsifiers such as di-isopropyl adipate, hexylene glycol, cetyl alcohol, stearyl alcohol, thickeners such as methyl cellulose, ethyl cellulose, hydroxymethylcellulose, hydroxypropylcellulose, polyvinylpyrrolidone, polyvinyl alcohol, and acrylic polymers. The topical formulation may include isopropyl alcohol. The isopropyl alcohol may be present in the formulation between about 1 wt % to about 40 wt %. Additionally the topical formulation may also include di-isopropyl adipate and hexylene glycol. The di-isopropyl adipate may be present in the formulation between about 1 wt % to about 10 wt %. The hexylene glycol may be present in the formulation between about 1 wt % to about 15 wt %. In addition the topical formulation may include polyoxyl 35 castor oil. The polyoxyl 35 castor oil may be present in the formulation from about 0 wt % to about 10 wt %. The formulation may also include at least one moisturizer/humectant. Other examples of suitable excipients, such as binders and fillers are listed in Remington's Pharmaceutical Sciences, 18th Edition, Ed. Alfonso Gennaro, Mack Publishing Co. Easton, Pa., 1995 and Handbook of Pharmaceutical Excipients, 3rd Edition, Ed. Arthur H. Kibbe, American Pharmaceutical Association, Washington D.C. 2000.

The topical formulations of the present disclosure may also include one or more skin care actives. "Skin care actives" means all compounds or substances now known or later demonstrated to provide benefit when applied to skin and all compounds now claimed or in the future claimed to provide benefit when applied to skin. Skin care actives may provide benefits, or claimed benefits, in areas such as one or more of wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-aging, reduction or avoidance of irritation, and reduction or avoidance of inflammation. Examples of skin care actives include molecules such as peptides, proteins, oligonucleotides, fullerenes as well as small molecules. Skin care actives may be protease and/or enzyme inhibitors, anti-coenzymes, chelating agents, antibodies, antimicrobials, humectants, vitamins, skin protectants, antioxidants and/or skin soothing agents, plant extracts and the like. Examples of skin care actives include but are not limited to vitamin C, vitamin E (alpha tocopherol), retinoids, soy derivatives (e.g. isoflavones), green tea polyphenols, alpha hydroxy acids (e.g. glycolic and lactic acids), beta hydroxy acids (e.g. salicylic acid), poly hydroxy acids, alpha lipoic acid, hemp oil (glycerides), niacinamide, dimethyl amino ethanol, coenzyme Q10, kinetin (plant growth hormone), dimethyl sulfone, and botulinum toxin. Other examples of skin care actives may be found in The Perricone Prescription by Nicholas Perricone, Harper Collins Publishers Inc., New York, 2002.

The topical formulation of the present invention may be formulated to be included in transdermal systems such as those described above, the topical formulations of the present invention may be formulated by those skilled in the art as liquids, solutions, emulsions, creams, lotions, suspensions, triturates, gels, jellies, foams, pastes, sprays, ointments, shampoos, adhesives, traditional patches, or the like.

The present formulation provides an improved topical formulation for facilitating topical or transdermal administration of at least one therapeutically active agent, which in accordance with examples herein, can be a corticosteroid. This enhanced effect is discussed further below and illustrated in embodiments of the formulations described in the Examples. In another example, the topical formulations provide a means for targeting a therapeutically active agent to a local tissue either in the skin or the underlying tissue. This latter embodiment may be particularly beneficially applied for treatment of conditions such as psoriasis and other dermatological conditions. The topical formulations may be applied either occlusively or nonocclusively to the skin. In a one embodiment, when the objective is transdermal administration, the topical formulation is applied to the skin under occlusion in a transdermal patch.

The present topical formulation may be applied to the skin by any means known in the art including, but not limited to, by an aerosol, spray, pump-pack, brush, swab, or other applicator. The applicator may provide either a fixed or variable metered dose application such as a metered dose aerosol, a stored-energy metered dose pump, or a manual metered dose pump. In this example, the topical formulation can be applied to the skin of the human or animal covering a delivery surface area from about 5 $cm^2$ to about 800 $cm^2$, more typically from about 10 $cm^2$ to about 400 $cm^2$, and in another example, from about 10 $cm^2$ to about 200 $cm^2$. The application can be performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. The drug delivery system may be a unit volume dispenser with or without a roll-on or other type of applicator. It may also be desirable to apply a number of dosages on untreated skin to obtain the desired result.

While the present disclosure is directed primarily to the formulations and related methods utilizing corticosteroids as the pharmaceutically active agent (drug), in some aspects, it can be useful or desirable to include alternative or additional pharmaceutically active compositions. Discussion of the various active agents that can be incorporated into the topical formulations, in addition to or instead of the corticosteroids of the present disclosure, is provided below.

In one aspect of the present invention, the at least one active agent is an aryl alkanoic acid, such as an α-aryl alkanoic acid. As is known to a person skilled in the art, α-aryl alkanoic acids are chemical compounds having the general structure of Formula II:

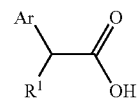

II wherein Ar is an aryl group and $R^1$ is H or an alkyl group, wherein aryl includes aromatic and heteroaromatic groups and alkyl includes acyclic and cyclic alkyl groups. The α-aryl alkanoic acid may be an anti-inflammatory drug such as a non-steroidal anti-inflammatory drug (NSAID) or an analagesic, specific examples of which are listed below. Preferably, the α-aryl alkanoic acids is selected from the group consisting of bromfenac, diclofenac, fenoprofen, flurbiprofen, ibuprofen, indomethacin, ketoprofen, ketorolac, naproxen, sulindac and tolmetin, and pharmaceutically acceptable salts and solvates thereof, and mixtures thereof. Structures for these α-aryl alkanoic acids, along with some common trade names, known to a person skilled in the art, are shown in Table A.

TABLE A

| NSAID | TRADE NAME | STRUCTURE |
|---|---|---|
| Diclofenac | Voltaren, Pennsaid | 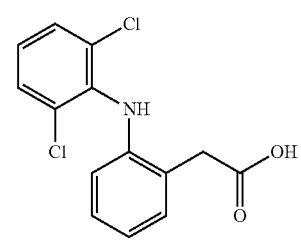 [SMILES: O=C(O)Cc1ccccc1Nc1c(Cl)cccc1Cl] |
| Indomethacin | Indocin | 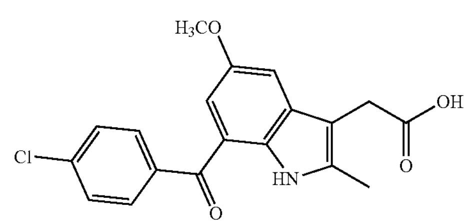 [SMILES: COc1cc(C(=O)c2ccc(Cl)cc2)c2[nH]c(C)c(CC(=O)O)c2c1] |
| Sulindac | Clinoril | 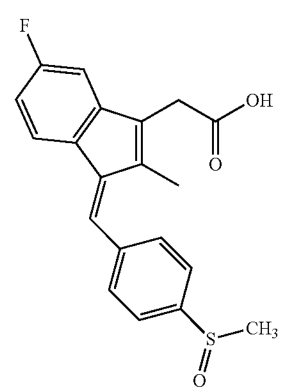 [SMILES: CC1=C(CC(=O)O)c2cc(F)ccc2/C1=C/c1ccc(S(C)=O)cc1] |

TABLE A-continued

| NSAID | TRADE NAME | STRUCTURE |
| --- | --- | --- |
| Tolmetin | Tolectin | 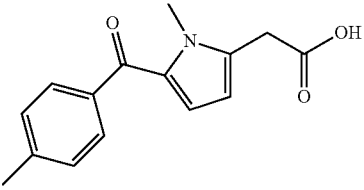 [SMILES: Cc1ccc(C(=O)c2ccc(CC(=O)O)n2C)cc1] |
| Naproxen | Naprosyn, Aleve | 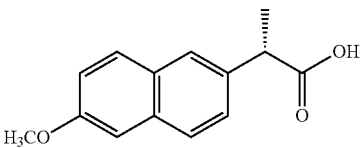 [SMILES: COc1ccc2cc([C@H](C)C(=O)O)ccc2c1] |
| Ibuprofen | Advil, Brufen, Motrin | 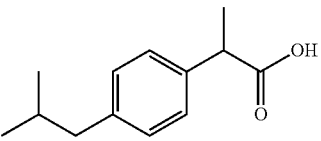 |
| Flurbiprofen | Ansaid, Flurwood, Froben | 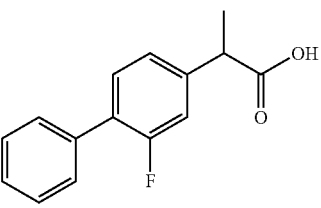 [SMILES: CC(C(=O)O)c1ccc(-c2ccccc2)c(F)c1] |
| Ketoprofen | Orudis | 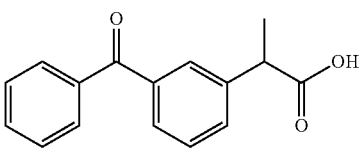 [SMILES: CC(C(=O)O)c1cccc(C(=O)c2ccccc2)c1] |
| Ketorolac | Acular, Toradol | 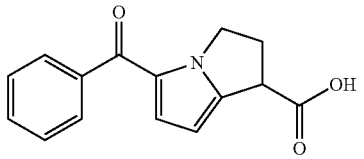 [SMILES: O=C(c1ccccc1)c1ccc2n1CCC2C(=O)O] |
| Fenoprofen | Nalfon | 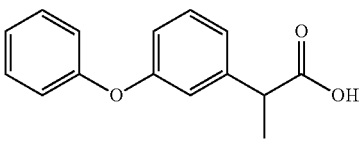 [SMILES: CC(C(=O)O)c1cccc(Oc2ccccc2)c1] |
| Bromfenac | Xibrom | 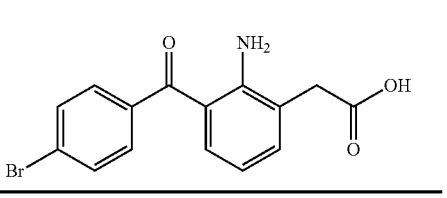 |

More preferably the α-aryl alkanoic acid is selected from the group consisting of diclofenac, ibuprofen, and ketoprofen, and pharmaceutically acceptable salts and solvates thereof, and mixtures thereof. Other NSAIDs that are not α-aryl alkanoic acids, as well as other compounds having antipyretic and analgesic actions are also included in the scope of the present invention. Examples of such compounds include acetaminophen (paracetamol), aspirin, celecoxib, diflunisal, etodolac, etoricoxib, meclofenamic acid, mefenamic acid, meloxicam, nabumetone, oxaprozin, piroxicam, salsalate, and rofecoxib. Structures for these compounds along with some common trade names, known to a person skilled in the art, are shown in Table B.

TABLE B
| COMPOUND | TRADE NAME | STRUCTURE |
| --- | --- | --- |
| Acetaminophen | Tylenol | 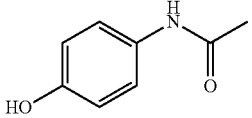 |
| Aspirin | | 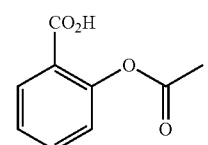 |
| Celecoxib | Celebrex | 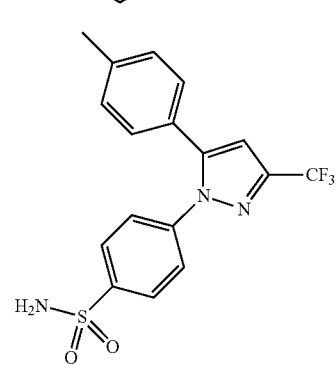 |
| Diflunisal | Dolobid | 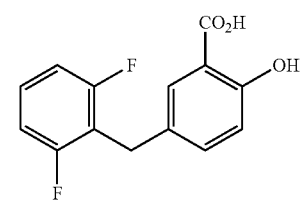 [SMILES: O=C(O)c1cc(Cc2c(F)cccc2F)ccc1O] |
| Etoricoxib | Arcoxia | 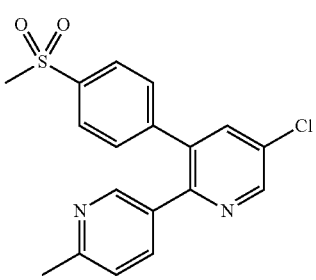 [SMILES: Cc1ccc(-c2ncc(Cl)cc2-c2ccc(S(C)(=O)=O)cc2)cn1] |
| Piroxicam | Feldane, Roxam | 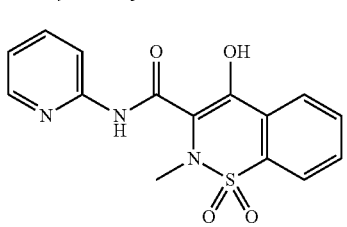 |
| Rofecoxib | Vioxx | 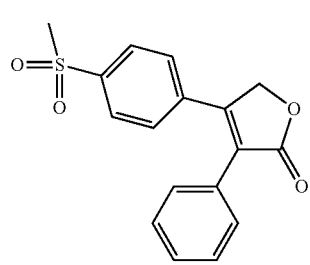 [SMILES: CS(=O)(=O)c1ccc(C2=C(c3ccccc3)C(=O)OC2)cc1] |

TABLE B-continued

| COMPOUND | TRADE NAME | STRUCTURE |
| --- | --- | --- |
| Salsalate | Disalcid, Monogesic, Salflex, Salcitab | 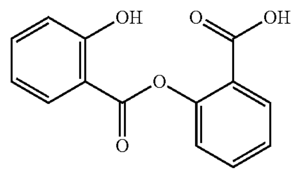 [SMILES: O=C(Oc1ccccc1C(=O)O)c1ccccc1O] |
| Meloxicam | Mobic | 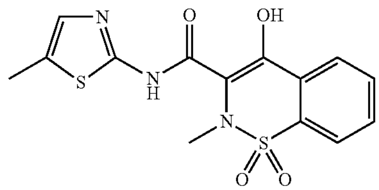 [SMILES: Cc1cnc(NC(=O)C2=C(O)c3ccccc3S(=O)(=O)N2C)s1] |
| Etodolac | Lodine | 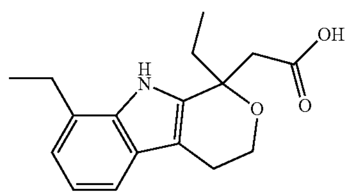 [SMILES: CCc1cccc2c3c([nH]c12)C(CC)(CC(=O)O)OCC3] |
| Oxaprozin | Daypro | 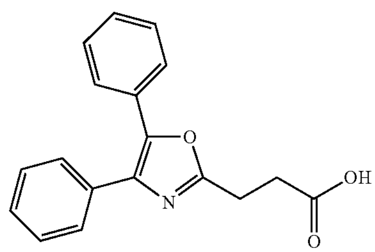 [SMILES: O=C(O)CCc1nc(-c2ccccc2)c(-c2ccccc2)o1] |
| Nabumetone | Relafen | 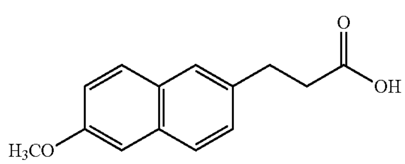 [SMILES: COc1ccc2cc(CCC(=O)O)ccc2c1] |
| Mefenamic acid | Ponstel | 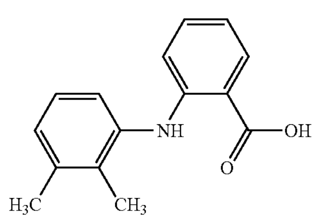 [SMILES: Cc1cccc(Nc2ccccc2C(=O)O)c1C] |
| Meclofenamic Acid | Meclofen, Meclomen | 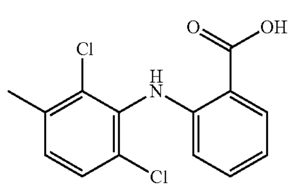 [SMILES: Cc1ccc(Cl)c(Nc2ccccc2C(=O)O)c1Cl] |

In another aspect of the present invention, the at least one active agent is a phenethylamine, for example, a phenethylamine that is an antidepressant, anti-anxiety agent, anticholinergic agent, cholinergic, dopaminergic, stimulant, serotonin antagonist, serotonin inhibitor, anti-emetic, antihistamine and/or antipsychotic, specific examples of which are listed below. As is known to a person skilled in the art, phenethylamines are chemical compounds having the general core structure of Formula III:

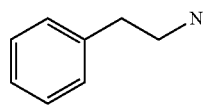

III wherein the phenyl ring, ethylene chain and nitrogen can be substituted. The phenethylamine may be a psychoactive agent that exerts its effect through a monoamine neurotransmitter system, for example dopamine, serotonin and/or norepinephrine receptors. Examples of phenethylamines, include, for example, bupropion, amphetamine, hydroxyamphetamine, dextroamphetamine, methamphetamine, ephedrine, epinephrine, pseudoephedrine, dopamine, epinephryl borate, etafedrine, norepinephrine and oxidopamine, and pharmaceutically acceptable salts and solvates thereof, and mixtures thereof. Preferably the phenethylamine is bupropion, or a pharmaceutically acceptable salt or solvate thereof, such as bupropion hydrochloride. The structure of bupropion, known to a person skilled in the art, is:

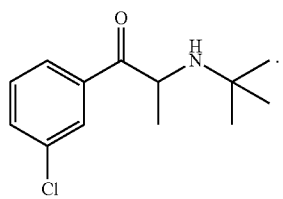

IV

In another aspect of the present invention, the at least one active agent is a steroid, other than coriticosteriods, for example, steroids that are hormones, glucosteroids, androgens, anabolics, estrogens and/or progestin, specific examples of which are listed below. Preferably the steroid is testosterone, or a pharmaceutically acceptable salt or solvate thereof.

Other suitable active agents include those in the class of COX-2 inhibitors such as celecoxib, rofecoxib, valdecoxib, lumiracoxib, etoricoxib; Antifungals such as tolnaftate, econazole, ciclopirox; Antibiotics such as clindamycin; Musculoskeletal agents such as dantrolene; Retinoids such as isotretinoin; Antivirals such as acyclovir; Vasodilating agents such as nitroglycerine, papaverine; Hormones and synthetic substitutes such as androgens, estrogens, insulin; Opiate agonists such as fentanyl, oxycodone, hydromorphone; Local Anaesthetics such as lidocaine, tocainide and mexiletine and butyl-para-aminobenzoate; NMDA receptor antagonists such as ketamine, dextromethorphan and amantadine.

Examples of other therapeutically active agents that may be used include the following: adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, anti-neutropenic, antiparasitic; antiproliferative; antipsychotic; antirheumatic; antiseborrheic; antisecretory; antispasmodic; antithrombotic; antiulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid suppressant; gastrointestinal motility effector; glucocorticoid; hair growth stimulant; hemostatic; histamine H2 receptor antagonists; hormone; hypocholesterolemic; hypoglycemic, hypolipidemic; hypotensive; imaging agent; immunizing agent; immunomodulator; immunoregulator; immunostimulant; immunosuppressant, keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic, tranquilizer; amyotrophic lateral sclerosis agent; cerebral ischemia agent; Paget's disease agent; unstable angina agent; vasoconstrictor; vasodilator; wound healing agent; xanthine oxidase inhibitor; and the like.

Specific examples of pharmaceutical agents that may be included within the present topical formulation, both alone or in combination, include but are not limited to:

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; and Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; and Tipredane.

Adrenocortical suppressant: Aminoglutethimide; and Trilostane.

Alcohol deterrent: Disulfiram.

Aldosterone antagonist: Canrenoate Potassium; Canrenone; Dicirenone; Mexrenoate Potassium; Prorenoate Potassium; and Spironolactone.

Amino acid: Alanine; Arginine; Aspartic Acid; Carnitine; Cysteine Hydrochloride; Cystine; Glycine; Histidine; Isoleucine; Leucine; Lysine; Lysine Acetate; Lysine Hydrochloride; Methionine; Phenylalanine; Proline; Serine; Threonine; Tryptophan; Tyrosine; and Valine.

Ammonia detoxicant: Arginine Glutamate; and Arginine Hydrochloride.

Amyotrophic lateral sclerosis agents: Riluzole.

Anabolic: Bolandiol Dipropionate; Bolasterone; Boldenone Undecylenate; Bolenol; Bolmantalate; Ethylestrenol; Methenolone Acetate; Methenolone Enanthate; Mibolerone; Nandrolone Cyclotate; Norbolethone; Pizotyline; Quinbolone; Stenbolone Acetate; Tibolone; and Zeranol.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carb aspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zomepirac Sodium; and Zucapsaicin.

Androgen: Fluoxymesterone; Mesterolone; Methyltestosterone; Nandrolone Decanoate; Nandrolone Phenpropionate; Nisterime Acetate; Oxandrolone; Oxymetholone; Silandrone; Stanozolol; Testosterone; Testosterone Cypionate; Testosterone Enanthate; Testosterone Ketolaurate; Testosterone Phenylacetate; Testosterone Propionate; and Trestolone Acetate.

Anesthesia (adjunct to): Sodium Oxybate.

Anesthetic: Aliflurane; Benoxinate Hydrochloride; Benzocaine; Biphenamine Hydrochloride; Bupivacaine Hydrochloride; Butamben; Butamben Picrate; Chloroprocaine Hydrochloride; Cocaine; Cocaine Hydrochloride; Cyclopropane; Desflurane; Dexivacaine; Diamocaine Cyclamate; Dibucaine; Dibucaine Hydrochloride; Dyclonine Hydrochloride; Enflurane; Ether; Ethyl Chloride; Etidocaine; Etoxadrol Hydrochloride; Euprocin Hydrochloride; Fluroxene; Halothane; Isobutamben; Isoflurane; Ketamine Hydrochloride; Levoxadrol Hydrochloride; Lidocaine; Lidocaine Hydrochloride; Mepivacaine Hydrochloride; Methohexital Sodium; Methoxyflurane; Midazolam Hydrochloride; Midazolam Maleate; Minaxolone; Norflurane; Octodrine; Oxethazaine; Phencyclidine Hydrochloride; Pramoxine Hydrochloride; Prilocaine Hydrochloride; Procaine Hydrochloride; Propanidid; Proparacaine Hydrochloride; Propofol; Propoxycaine Hydrochloride; Pyrrocaine; Risocaine; Rodocaine; Roflurane; Salicyl Alcohol; Sevoflurane; Teflurane; Tetracaine; Tetracaine Hydrochloride; Thiamylal; Thiamylal Sodium; Thiopental Sodium; Tiletamine Hydrochloride; and Zolamine Hydrochloride.

Anorectic compound: Dexfenfluramine.

Anorexic agents: Aminorex; Amphecloral; Chlorphentermine Hydrochloride; Clominorex; Clortermine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phemnetrazine Hydrochloride; Phentermine; and Sibutramine Hydrochloride.

Antagonist: Atipamezole; Atosiban; Bosentan; Cimetidine; Cimetidine Hydrochloride; Clentiazem Maleate; Detirelix Acetate; Devazepide; Donetidine; Etintidine Hydrochloride; Famotidine; Fenmetozole Hydrochloride; Flumazenil; Icatibant Acetate; Icotidine; Isradipine; Metiamide; Nadide; Nalmefene; Naloxone Hydrochloride; Naltrexone; Nilvadipine; Oxilorphan; Oxmetidine Hydrochloride; Oxmetidine Mesylate; Quadazocine Mesylate; Ranitidine; Ranitidine Bismuth Citrate; Ranitidine Hydrochloride; Sufotidine; Teludipine Hydrochloride; Tiapamil Hydrochloride; Tiotidine; Vapiprost Hydrochloride; and Zaltidine Hydrochloride.

Anterior pituitary activator: Epimestrol.

Anterior pituitary suppressant: Danazol.

Anthelmintic: Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; Piperazine; Piperazine Citrate; Piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Triclofenol Piperazine; Vincofos; and Zilantel.

Anti-acne: Adapalene; Erythromycin, Salnacedin; and Inocoterone Acetate.

Anti-adrenergic: Acebutolol; Alprenolol Hydrochloride; Atenolol; Bretylium Tosylate; Bunolol Hydrochloride; Carteolol Hydrochloride; Celiprolol Hydrochloride; Cetamolol Hydrochloride; Cicloprolol Hydrochloride; Dexpropranolol Hydrochloride; Diacetolol Hydrochloride; Dihydroergotamine Mesylate; Dilevalol Hydrochloride; Esmolol Hydrochloride; Exaprolol Hydrochloride; Fenspiride Hydrochloride; Flestolol Sulfate; Labetalol Hydrochloride; Levobetaxolol Hydrochloride; Levobunolol Hydrochloride; Metalol Hydrochloride; Metoprolol; Metoprolol Tartrate; Nadolol; Pamatolol Sulfate; Penbutolol Sulfate; Phentolamine Mesylate; Practolol; Propranolol Hydrochloride; Proroxan Hydrochloride; Solypertine Tartrate; Sotalol Hydrochloride; Timolol; Timolol Maleate; Tiprenolol Hydrochloride; Tolamolol; and Zolertine Hydrochloride.

Anti-allergic: Amlexanox; Astemizole; Azelastine Hydrochloride; Eclazolast; Minocromil Nedocromil Nedocromil Calcium; Nedocromil Sodium; Nivimedone Sodium; Pemirolast Potassium Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; and Tixanox.

Anti-amebic: Berythromycin; Bialamicol Hydrochloride; Chloroquine; Chloroquine Hydrochloride; Chloroquine Phosphate; Clamoxyquin Hydrochloride; Clioquinol; Emetine Hydrochloride; Iodoquinol; Paromomycin Sulfate; Quinfamide; Symetine Hydrochloride; Teclozan; Tetracycline; and Tetracycline Hydrochloride.

Anti-androgen: Benorterone; Cioteronel; Cyproterone Acetate; Delmadinone Acetate; Oxendolone; Topterone; and Zanoterone.

Anti-anemic: Epoetin Alfa; Epoetin Beta; Ferrous Sulfate, Dried; and Leucovorin Calcium.

Anti-anginal: Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; and Verapamil Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; and Zalospirone Hydrochloride.

Anti-arthritic: Lodelaben.

Anti-asthmatic: Ablukast; Ablukast Sodium; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Ritolukast; Sulukast; Tiaramide Hydrochloride; Tibenelast Sodium; Tomelukast; Tranilast; Verlukast; and Verofylline Zarirlukast.

Anti-atherosclerotic: Mifobate; and Timefuronc.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylate sodium; Aminosalicylic acid; Amoxicillin; Amphomycin; Ampicillin; Ampicillin Sodium; Apalcillin Sodium; Apramycin; Aspartocin; Astromicin Sulfate; A vilamycin; A voparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Betamicin Sulfate; Biapenem; Biniramycin; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftiroxime Pivoxetil; Ceftizoxime Sodium; Ceftriaxone Sodium; Cefuroxime; Cefuroxime Axetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isepamicin; Isoconazole; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifarthiazole; Nifuradene; Nifuraldezone; Nifuratel; Nifuratrone; Nifurdazil; Nifurimide; Nifurpirinol; Nifurquinazol; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-cancer supplementary potentiating agents: Amitryptyline; Amoxapine; Amphotericin B; Antiarrhythmic drugs (e.g., Quinidine); Antihypertensive drugs (e.g., Reserpine); Ca++ antagonists (e.g., Verapamil; Calmodulin inhibitors (e.g., Prenylamine; Caroverine); Citalopram); Clomipramine; Clomipramine); Desipramine; Doxepin; Maprotiline); Nifedipine; Nitrendipine; Non-tricyclic anti-depressant drugs (e.g., Sertraline; Nortriptyline; Protriptyline; Sulfoximine) and Multiple Drug Resistance reducing agents such as Cremaphor EL; Thiol depleters (e.g., Buthionine; Trazodone; Tricyclic anti-depressant drugs (e.g., Imipramine; Trifluoroperazine; Trimipramine; and Triparanol analogues (e.g., Tamoxifen).

Anticholelithic: Monoctanoin.

Anticholelithogenic: Chenodiol; Ursodiol.

Anticholinergic: Alverinc Citrate; Anisotropine Methylbromide; Atropine; Atropine Oxide Hydrochloride; Atropine Sulfate; *Belladonna*; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; and Tropicamide.

Anticoagulant: Ancrod; Ardeparin Sodium; Bivalirudin; Bromindione; Dalteparin Sodium Desirudin; Dicumarol; Lyapolate Sodium; Nafamostat Mesylate; Phenprocoumon; Tinzaparin Sodium; and Warfarin Sodium.

Anticoccidal: Maduramicin.

Anticonvulsant: Albutoin; Ameltolide; Atolide; Buramate; Cinromide; Citenamide; Clonazepam; Cyheptamide; Dezinamide; Dimethadione; Divalproex Sodium; Eterobarb; Ethosuximide; Ethotoin; Flurazepam Hydrochloride; Fluzinamide; Fosphenytoin Sodium; Gabapentin; Ilepcimide; Lamotrigine; Magnesium Sulfate; Mephenytoin; Mephobarbital; Methetoin; Methsuximide; Milacemide Hydrochloride; Nabazenil; Nafimidone Hydrochloride; Nitrazepam; Phenacemide; Phenobarbital; Phenobarbital Sodium; Phensuximide; Phenytoin; Phenytoin Sodium; Primidone; Progabide; Ralitoline; Remacemide Hydrochloride; Ropizine; Sabeluzole; Stiripentol; Sulthiame; Topiramate; Trimethadione; Valproate Sodium; Valproic Acid; Vigabatrin; Zoniclezole Hydrochloride; and Zonisamide.

Antidepressant: Adinazolam; Adinazolam Mesylate; Alaproclate; Aletamine Hydrochloride; Amedalin Hydrochloride; Amitriptyline Hydrochloride; Aptazapine Maleate; Azaloxan Fumarate; Azepindole; Azipramine Hydrochloride; Bipenamol Hydrochloride; Bupropion Hydrochloride; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pridefine Hydrochloride; Prolintane Hydrochloride; Protriptyline Hydrochloride; Quipazine Maleate; Rolicyprine; Seproxetine Hydrochloride; Sertraline Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine Maleate; Venlafaxine Hydrochloride; Viloxazine Hydrochloride; Zimeldine Hydrochloride; and Zometapine.

Antidiabetic: Acetohexamide; Buformin; Butoxamine Hydrochloride; Camighbose; Chlorpropamide; Ciglitazone; Englitazone Sodium; Etoformin Hydrochloride; Gliamilide; Glibornuride; Glicetanile Sodium; Gliflumide; Glipizide; Glucagon; Glyburide; Glyhexamide; Glymidine Sodium; Glyoctamide; Glyparamide; Insulin; Insulin Human; Insulin Human Zinc; Insulin Human Zinc, Extended; Insulin Human, Isophane; Insulin Lispro; Insulin Zinc; Insulin Zinc, Extended; Insulin Zinc, Prompt; Insulin, Dalanated; Insulin, Isophane; Insulin, Neutral; Linogliride; Linogliride Fumarate; Metformin; Methyl Palmoxirate; Palmoxirate Sodium; Pioglitazone Hydrochloride; Pirogliride Tartrate; Proinsulin Human; Seglitide Acetate; Tolazamide; Tolbutamide; Tolpyrramide; Troglitazone; and Zopolrestat.

Antidiarrheal: Diphenoxylate Hydrochloride; Methylprednisolone; Metronidazole; and Rolgamidine.

Antidiuretic: Argipressin Tannate; Desmopressin Acetate; and Lypressin.

Antidote: Dimercaprol; Edrophonium Chloride; Fomepizole; Levoleucovorin Calcium; Methylene Blue; and Protamine Sulfate.

Antidyskinetic: Selegiline Hydrochloride.

Anti-emetic: Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Flumeridone; Galdansetron Hydrochloride; Granisetron; Granisetron Hydrochloride; Lurosetron Mesylate; Meclizine Hydrochloride; Metoclopramide Hydrochloride; Metopimazine; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; and Zacopride Hydrochloride.

Anti-epileptic: Felbamate; Iamotrigine; Loreclezole; and Tolgabide.

Anti-estrogen: Clometherone; Nafoxidine Hydrochloride; Nitromifene Citrate; Raloxifene Hydrochloride; Tamoxifen Citrate; Toremifene Citrate; and Trioxifene Mesylate.

Antifibrinolytic: Nafamostat Mesylate.

Antifungal: Acrisorcin; Ambruticin; Azaconazole; Azaserine; Basifungin; Bifonazole; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Itraconazole; Kalafungin; Ketoconazole; Lomoftmgin; Lydimycin; Mepartricin; Miconazole; Miconazole Nitrate; Monensin; Monensin Sodium; Naftifine Hydrochloride; Nifuratel Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Pyrrolnitrin; Rutamycin; Sanguinarium Chloride; Saperconazole; Selenium Sulfide; Sinefungin; Sulconazole Nitrate; Terbinafine; Terconazole; Thiram; Tioconazole; Tolciclate; Tolindate; Tolnaftate; Triacetin; Triafungin; Undecylenic Acid; Viridofulvin; Zinc Undecylenate; and Zinoconazole Hydrochloride.

Antiglaucoma agent: Alprenoxime Hydrochloride; Colforsin; Dipivefrin Hydrochloride; Naboctate Hydrochloride; Pilocarpine; and Pirnabine.

Antihemorrhagic: Poliglusam.

Antihemorrheologic: Phentoxifylline.

Antihistaminic: Acrivastine; Antazoline Phosphate; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cirmarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Fexofenadine HCI; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; and Triprolidine Hydrochloride.

Antihyperlipidemic: Cholestyramine Resin; Clofibrate; Colestipol Hydrochloride; Crilvastatin; Dalvastatin; Dextrothyroxine Sodium; Fluvastatin Sodium; Gemfibrozil; Lecimibide; Lovastatin; Niacin; Pravastatin Sodium; Probucol; Simvastatin; Tiqueside; and Xenbucin.

Antihyperlipoproteinemic: Acifran; Beloxamide; Bezafibrate; Boxidine; Cetaben Sodium; Ciprofibrate; Gemcadiol; Halofenate; Lifibrate; Meglutol; Nafenopin; Pimetine Hydrochloride; Theofibrate; Tibric Acid; and Treloxinate.

Antihypertensive: Alfuzosin Hydrochloride; Alipamide; Althiazide; Amiquinsin Hydrochloride; Anaritide Acetate; Atiprosin Maleate; Belfosdil; Bemitradine; Bendacalol Mesylate; Bendroflumethiazide; Benzthiazide; Bethanidine Sulfate; Biclodil Hydrochloride; Bisoprolol; Bisoprolol Fumarate; Bucindolol Hydrochloride; Bupicomide; Buthiazide; Candoxat rilat; Candoxatril; Captopril; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Diltiazem Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancvdine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxvfen Sulfate; Hydralazine Hydrochloride; Hydralazine Polistirex; Hydroflumethiazide; Indacrinone Indapamide; Indolapril Hydrochloride; Indoramin; Indoramin Hydrochloride; Indorenate Hydrochloride; Lacidipine; Leniquinsin; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide Methyclothiazide Methyldopa; Methyldopate Hydrochloride; Metipranolol; Metolazone Metoprolol Fumarate; Metyrosine; Minoxidil; Muzolimine; Nebivolol; Nifidipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia *Serpentina*; Reserpine; Saprisartan Potassium; Saralasin Acetate; Sodium Nitroprusside; Sulfinalol Hydrochloride; Tasosartan; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; and Zofenoprilat Arginine.

Antihypotensive: Ciclafrine Hydrochloride; and Midodrine Hydrochloride.

Anti-infective: Acyclovir; Difloxacin Hydrochloride; Integrase Inhibitors of HIV and other retroviruses; Lauryl Isoquinolinium Bromide; Moxalactam Disodium; Ornidazole; Pentisomicin; Protease inhibitors of HIV and other retroviruses; and Sarafloxacin Hydrochloride.

Anti-infective (topical): Alcohol; Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofarazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; and Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anitrazafen; Apazone; Balsalazide Disodium; Bendazac; Bromelains; Broperamole; Budesonide; Carprofen; Ciclopirofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Difluprednate; Diftalone; Dimethyl Sulfoxide; Drocinonide; Endrysone; Enlimomab; Enolicam Sodium; Etodolac; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Fluocortin Butyl; Fluorometholone Acetate; Fluquazone; Fluretofen; Fluticasone Propionate; Furaprofen; Furobufen; Halcinonide; Halobetasol Propionate; Halopredone Acetate; Ibuprofen; Ibuprofen Aluminum; Ibuprofen Piconol; Ilonidap; Indomethacin Sodium; Indomethacin; Indoprofen Indoxole; Intrazole; Isoflupredone Acetate; Isoxepac; Isoxicam; Ketoprofen; Lomoxicam; Loteprednol Etabonate; Meclofenamate Sodium; Meclofenamic Acid; Meclorisonc Dibutyrate; Mesalamine; Meseclazone; Methylprednisolone Suleptanate; Morniflumate; Nabumetone; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Pirprofen; Prednazate; Prednisolone Sodium Phosphate; Prifelone; Prodolic Acid; Proquazone; Rimexolone; Romazarit; Salnacedin; Seclazone; Sermetacin; Sudoxicam; Sulindac; Suprofen; Talniflumate; Tenidap; Tenidap Sodium; Tenoxicam; Tesicam; Tesimide; Tixocortol Pivalate; Tolmetin; Tolmetin Sodium; Triclonide; Triflumidate; and Zidometacin.

Antikeratinizing agent: Doretinel; Linarotene; and Pelretin.

Antimalarial: Amodiaquine Hydrochloride; Amquinate; Artefiene; Chloroquine; Chloroquine Hydrochloride; Cycloguanil Pamoate; Enpiroline Phosphate; Halofantrine Hydrochloride; Hydroxychloroquine Sulfate; Mefloquine Hydrochloride; Menoctone; Primaquine Phosphate; Pyrimethamine; Quinine Sulfate; and Tebuquine.

Antimicrobial: Aztreonam; Chlorhexidine Gluconate; Imidurea; Lycetamine; Nibroxane; Pirazmonam Sodium; Propionic Acid; Pyrithione Sodium; and Tigemonam Dicholine.

Antimigraine: Naratriptan Hydrochloride; Sergolexole Maleate; Sumatriptan Succinate; and Zatosetron Maleate.

Antimitotic: Podofilox.

Antimycotic: Amorolfine.

Antinauseant: Buclizine Hydrochloride; and Cyclizine Lactate.

Antineoplastic: Acivicin; Aclarubicin; Acodazole Hydrochloride; Acronine; Adozelesin; Aldesleukin; Altretamine; Ambomycin; Ametantrone Acetate; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cisplatin; Cladribine; Crisnatol Mesylate; Cyclophosphamide; Cytarabine; Dacarbazine; Dactinomycin; Daunorubicin Hydrochloride; Decitabine; Dexorinaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin, Hydrochloride; Ifosfamide; Ilmofosine; Interferon Alfa-2a; Interferon Alfa-2b; Interferon Alfan3; Interferon Alfa-nl; Interferon Beta-I a; Interferon Garmna-I b; Iproplatin; Irinotecan Hydrochloride; Isotretinoin; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamvcin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Prednimustine; Procarbazine Hydrochloride; Puromycin; Puromycin Hydrochloride; Pyrazofurin; Riboprine; Rogletimide; Safingol Safingol Hydrochloride; Semustine; Simtrazene; Sparfosate Sodium; Sparsomycin; Spiro germanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofarin; Tirapazamine; Topotecan Hydrochloride; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Anti-neoplastic compounds (additional): 20-epi-1,25 Dihydroxyvitamin D3; 5-Ethynyluracil; Abiraterone; Acylfulvene; Adecypenol; ALL-TK Antagonists; Ambamustine; Amidox; Amifostine; Aminolevulinic Acid; Amrubicin; Anagrelide; Andrographolide; Angiogenesis Inhibitors; Antagonist D; Antagonist G; Antarelix; Antiandrogen, Prostatic Carcinoma; Anti-Dorsalizing Morphogenetic Protein-I; Antiestrogen; Antineoplaston; Antisense Oligonucleotides; Aphidicolin Glycinate; Apoptosis Gene Modulators; Apoptosis Regulators; Apurinic Acid; Ara-CDP-DL-PTBA; Arginine Deaminase; Asulacrine; Atamestane; Atrimustine; Axinastatin 1; Axinastatin 2; Axinastatin 3; Azasetron; Azatoxin; Azatyrosine; Baccatin III Derivatives; Balanol; BCR/ABL Antagonists; Benzochlorins; Benzoylstaurosporine; Beta Lactam Derivatives; Beta-Alethine; Betaclamycin B; Betulinic Acid; bFGF Inhibitor; Bisantrene; Bisaziridinylspermine; Bisnafide; Bistratene A; Breflate; Budotitane; Buthionine Sulfoximine; Calcipotriol; Calphostin C; Camptothecin Derivatives; Canarypox IL-2; Capecitabine; Carboxamide-Amino-Triazole; Carboxyamidotriazole; CaRest MI; CARN 700, Cartilage Derived Inhibitor; Casein Kinase Inhibitors (ICOS); Castanospermine; Cecropin B; Cetrorelix; Chlorins; Chloroquinoxaline Sulfonamide; Cicaprost; Cis-Porphyrin; Clomifene analogues; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacliximab; Dehydrodidenmin B; Dexifosfamide; Dexverapamil; Didemnin B; Didox; Diethylnorspennine; Dihydro Azacytidine; 9-Dihydrotaxol; Dioxamycin; Diphenyl Spiromustine; Docosanol; Dolasetron; Doxifluridine; Duocarmycin SA; Ebselen; Ecomustine; Edelfosine; Edrecolomab; Eflomithine; Elemene; Emitefur; Epirubicin; Estramustine Analogue; Estrogen Agonists; Estrogen Antagonists; Exemestane; Fadrozole; Fiezelastine; Flavopiridol; Fluasterone; Fludarabine; Fluorodaunorunicin Hydrochloride; Forfenimex; Formestane; Fostriecin; Fotemustine; Gadolinium Texaphyrin; Gallium Nitrate; Galocitabine; Ganirelix; Gelatinase Inhibitors; Glutathione Inhibitors; Hepsulfam; Heregulin; Hexamethylene Bisacetamide; Hypericin; Ibandronic acid; Idarubicin; Idoxifene; Idramantone; Ilomastat; Imidazoacridones; Immunostimulant Peptides; Insulin-Like Growth Factor-1 Receptor Inhibitor; Interferon Agonists; Interferons; Interleukins; Iobenguane; Iododoxorubicin; 4-Ipomeanol; Irinotecan; Iroplact; Irsogladine; Isobengazole; Isohomohalicondrin B; Itasetron; Jasplakinolide; Kahalalide F; Lamellarin-N Triacetate; Lanreotide; Leinamycin; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lurtotecan; Lutetium Texaphyrin; Lysofylline; Lytic Peptides; Maitansine; Mannostatin A; Marimastat; Maspin; Matrilysin Inhibitors; Matrix Metalloproteinase Inhibitors; Merbarone; Meterelin; Methioninase; Metoclopramide; MIF Inhibitor; Mifepristone; Miltefosine; Mirimostim; Mismatched Double Stranded RNA; Mitoguazone; Mitolactol; Mitomycin analogues; Mitonafide; Mitotoxin Fibroblast Growth Factor-Saporin; Mitoxantrone; Mofarotene; Monoclonal Antibody, Human Chorionic Gonadotrophin; Monophosphoryl Lipid A+Myobacterium Cell Wall Sk; Mopidamol; Multiple Drug Resistance Gene Inhibitor; Multiple Tumor Suppressor I-Based Therapy; Mustard Anticancer Agent; Mycaperoxide B; Mycobacterial Cell Wall Extract; Myriaporone; NAcetyldinaline; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; N-Substituted Benzamides; 06-Benzylguanine; Okicenone; Oligonucleotides; Onapristone; Ondansetron; Oracin; Oral Cytokine Inducer; Osaterone; Oxaliplatin; Oxaunomycin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentostatin; Pentrozole; Perflubron; Perillyl Alcohol; Phenazinomycin; Phenylacetate; Phosphatase Inhibitors; Picibanil; Pilocarpine Hydrochloride; Pirarubicin; Piritrexim; Placetin A; Placetin B; Plasminogen Activator Inhibitor; Platinum Complex; Platinum Compounds; Platinum-Triamine Complex; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin Polyoxyethylene Conjugate; Raf Antagonists; Raltitrexed; Ramosetron; Ras Famesyl Protein Transferase Inhibitors; Ras Inhibitors; Ras-GAP Inhibitor; Retelliptine Demethylated; Rhenium, Re 186 Etidronate; Rhizoxin; Ribozymes; Rh Retinamide; Rohitukine; Romurtide; Roquinimex; Rubiginone B 1; Ruboxyl; Safingol; Saintopin; SarCNU; Sarcophytol A; Sdi 1 Mimetics; Senescence Derived Inhibitor 1; Sense Oligonucleotides; Signal Transduction Inhibitors; Signal Transduction Modulators; Single Chain Antigen Binding Protein; Sizofiran; Sobuzoxane; Sodium Borocaptate; Sodium Phenylacetate; Solverol; Somatomedin Binding Protein; Sonermin; Sparfosic Acid; Spicamycin D; Splenopentin; Spongistatin 1; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Tallimustine; Tamoxifen Methiodide; Tauromustine; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Triacetyluridine; Triciribine; Tropisetron; Turosteride; Tyrosine Kinase Inhibitors; Tyrphostins; UBC Inhibitors; Ubenimex; Urogenital Sinus-Derived Growth Inhibitory Factor; Urokinase Receptor Antagonists; Variolin B; Vector system, Erythrocyte Gene Therapy;

Velaresol; Veramine; Verdins; Vinorelbine; Vinxaltine; Vitaxin; Zilascorb; and Zinostatin Stimalamer.

Antineutropenic: Filgrastim; Lenograstim; Molgramostim; Regramostim; and Sargramostim.

Antiobsessional agent: Fluvoxamine Maleate.

Antiparasitic: Abamectin; Clorsulon; and Ivermectin.

Antiparkinsonian: Benztropine Mesylate; Biperiden; Biperiden Hydrochloride; Biperiden Lactate; Carbidopa-Levodopa; Carmantadine; Ciladopa Hydrochloride; Dopamantine; Ethopropazine Hydrochloride; Lazabemide; Levodopa; Lometraline Hydrochloride; Mofegiline Hydrochloride; N axagolide Hydrochloride; Pareptide Sulfate; Procyclidine Hydrochloride; Ropinirole Hydrochloride; and Tolcapone.

Antiperistaltic: Difenoximide Hydrochloride; Difenoxin; Fluperamide; Lidamidine Hydrochloride; Loperamide Hydrochloride; Malethamer; Nufenoxole; Paregoric.

Antipneumocystic: Atovaquone.

Antiproliferative agent: Piritrexim Isethionate.

Antiprostatic hypertrophy: Sitogluside.

Antiprotozoal: Amodiaquine; Azanidazole; Banmidazole; Camidazole; Chlortetracycline Bisulfate Chlortetracycline Hydrochloride; Flubendazole; Flunidazole; Halofuginone Hydrobromide; Imidocarb Hydrochloride; Ipronidazole; Misonidazole; Moxnidazole; Nitarsone; Ronidazole; Sulnidazole; and Tinidazole.

Antipruritic: Methdilazine; Methdilazine Hydrochloride; and Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; and Tepoxalin.

Antipsychotic: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

Antirheumatic: Auranofin; Aurothioglucose; Bindarit; Lobenzarit Sodium; Phenylbutazone; Pirazolac; Prinomide Tromethamine; and Seprilose.

Antischistosomal: Becanthone Hydrochloride; Hycanthone; Lucanthone Hydrochloride; Niridazole; Oxamniquine; Pararosaniline Pamoate; and Teroxalene Hydrochloride.

Antiseborrheic: Chloroxine; Piroctone; Piroctone Olamine; and Resorcinol Monoacetate.

Antisecretory: Arbaprostil; Deprostil; Fenoctimine Sulfate; Octreotide; Octreotide Acetate; Omeprazole Sodium; Rioprostil; Trimoprostil.

Antispasmodic: Stilonium Iodide; Tizanidine Hydrochloride.

Antithrombotic: Anagrelide Hydrochloride; Dalteparin Sodium; Danaparoid Sodium; Dazoxiben Hydrochloride; Efegatran Sulfate; Enoxaparin Sodium; Ifetroban; Ifetroban Sodium; and Trifenagrel.

Antitussive: Benzonatate; Butamirate Citrate; Chlophedianol Hydrochloride; Codeine Polistirex; Codoxime; Dextromethorphan; Dextromethorphan Hydrobromide; Dextromethorphan Polistirex; Ethyl Dibunate; Guaiapate; Hydrocodone Bitartrate; Hydrocodone Polistirex; Levopropoxyphene Napsylate; Noscapine; Pemerid Nitrate; Pipazethate; and Suxemerid Sulfate.

Anti-ulcerative: Aceglutamide Aluminum; Cadexomer Iodine; Cetraxate Hydrochloride; Enisoprost; Isotiquimide; Lansoprazole; Lavoltidine Succinate; Misoprostol; Nizatidine; Nolinium Bromide; Pantoprazole; Pifarnine; Pirenzepine Hydrochloride; Rabeprazole Sodium; Remiprostol; Roxatidine Acetate Hydrochloride; Sucralfate; Sucrosofate Potassium; and Tolimidone.

Anti-urolithic: Cysteamine; Cysteamine Hydrochloride; and Tricitrates.

Antiviral: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Appetite suppressant: Dexfenfluramine Hydrochloride; Phendimetrazine Tartrate; and Phentermine Hydrochloride.

Benign prostatic hyperplasia therapy agent: Tamsulosin Hydrochloride.

Blood glucose regulators: Acetohexamide and Glipizide; Chloropropamide; and Human insulin.

Bone resorption inhibitor: Alendronate Sodium; Etidronate Disodium; and Pamidronate Disodium.

Bronchodilator: Albuterol; Albuterol Sulfate; Azanator Maleate; Bamifylline Hydrochloride; Bitolterol Mesylate; Butaprost; Carbuterol Hydrochloride; Clorprenaline Hydrochloride; Colterol Mesylate; Doxaprost; Doxofylline; Dyphylline; Enprofylline; Ephedrine; Ephedrine Hydrochloride; Fenoterol; Fenprinast Hydrochloride; Guaithylline; Hexoprenaline Sulfate; Hoquizil Hydrochloride; Ipratropium Bromide; Isoetharine; Isoetharine Hydrochloride; Isoetharine Mesylate; Isoproterenol Hydrochloride; Isoproterenol Sulfate; Metaproterenol Polistirex; Metaproterenol Sulfate; Nisbuterol Mesylate; Oxtriphylline; Picumeterol Fumarate; Piquizil Hydrochloride; Pirbuterol Acetate; Pirbuterol Hydrochloride; Procaterol Hydrochloride; Pseudoephedrine Sulfate; Quazodine; Quinterenol Sulfate; Racepinephrine; Racepinephrine Hydrochloride; Reproterol Hydrochloride; Rimiterol Hydrobromide; Salmeterol; Salmeterol Xinafoate; Soterenol Hydrochloride; Sulfonterol Hydrochloride; Suloxifen Oxalate; Terbutaline Sulfate; Theophylline; Xanoxate Sodium; Zindotrine; and Zinterol Hydrochloride.

Carbonic anhydrase inhibitor: Acetazolamide; Acetazolamide Sodium; Dichlorophenamide; Dorzolamide Hydrochloride; Methazolamide; and Sezolamide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; and Transcainide.

Cardioprotectant: Dexrazoxane; and Draflazine.

Cardiotonic agent: Actodigin; Amrinone; Bemoradan; Butopamine; Carbazeran; Carsatrin Succinate; Deslanoside; *Digitalis*; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; and Vesnarinone.

Cardiovascular agent: Dopexamine; and Dopexamine Hydrochloride.

Cerebral ischemia Dextrorphan Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostiamine Methylsulfate; Neostigmine Bromide; Physostigmine; Physostigmine Salicylate; Physostigmine Sulfate; Pilocarpine Nitrate; and Pyridostigmine Bromide.

Cholinergic agonist: Xanomeline; and Xanomeline Tartrate.

Cholinesterase Deactivator: Obidoxime Chloride; Pralidoxime Chloride; Pralidoxime Iodide; and Pralidoxime Mesylate.

Coccidiostat: Arprinocid; Narasin; Semduramicin; and Semduramicin Sodium.

Cognition adjuvant: Ergoloid Mesylates; Piracetam; Pramiracetam Hydrochloride; Pramiracetam Sulfate; and Tacrine Hydrochloride.

Cognition enhancer: Besipirdine Hydrochloride; Linopirdine; and Sibopirdine.

Contrast Media: Barium Sulfate; Diatrizoate Sodium; Erythrosine Sodium; Iopanoic Acid; Ipodate Calcium; Metrapone; and Tyropanoate Sodium.

Diagnostic aid: Aminohippurate Sodium; Anazolene Sodium; Arclofenin; Bentiromide; Benzylpenicilloyl Polylysine; Butedronate Tetrasodium; Butilfenin; Coccidioidin; Corticorelin Ovine Triflutate; Corticotropin Zinc Hydroxide; Corticotropin, Repository; Diatrizoate Meglumine; Diatrizoic Acid; Diphtheria Toxin for Schick Test; Disofenin; Ethiodized Oil; Etifenin; Exametazime; Ferristenc; Ferumoxides; Ferumoxsil; Fluorescein; Fluorescein Sodium; Gadobenate Dimeglumine; Gadodiamide; Gadopentetate Dimegiumine; Gadoteridol; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopentol; Iophendylate; Ioprocemic Acid; Iopronic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxagiate Sodium; Ioxaglate Meglumine; Ioxaglic Acid; Ioxilan; Ioxotrizoic Acid; Ipodate Sodium; Iprofenin; Isosulfan Blue; Leukocyte Typing Serum; Lidofenin; Mebrofenin; Meglumine; Metrizamide; Metrizoate Sodium; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; and Xylose.

Diuretic: Ambuphylline; Ambuside; Amiloride Hydrochloride; Azolimine; Azosemide; Brocrinat; Bumetanide; Chlorothiazide; Chlorthalidone; Clazolimine; Clorexolone; Ethacrynate Sodium; Ethacrynic Acid; Etozolin; Fenquizone; Furosemide; Hydrochlorothiazide; Isosorbide; Mannitol Mefruside; Ozolinone; Piretanide; Spiroxasone; Torsemide; Triamterene; Triflocin; and Urea.

Dopaminergic agent: Ibopamine.

Ectoparasiticide: Nifluridide; Permethrin.

Emetic: Apomorphine Hydrochloride.

Enzyme inhibitor: 30 Polignate Sodium; Acetohydroxamic Acid; Alrestatin Sodium; Aprotinin; Benazepril Hydrochloride; Benazeprilat; Benurestat; Bromocriptine; Bromocriptine Mesylate; Cilastatin Sodium; Flurofamide; Lergotrile; Lergotrile Mesylate; Levcycloserine; Libenzapril; Pentopril; Pepstatin; Perindopril; Sodium Amylosulfate; Sorbinil; Spirapril Hydrochloride; Spiraprilat; Taleranol; Teprotide; Tolfamide; and Zofenopril Calcium.

Estrogen: Chlorotrianisene; Dienestrol; Diethylstilbestrol; Diethylstilbestrol Diphosphate; Equilin; Estradiol; Estradiol Cypionate; Estradiol Enanthate; Estradiol Undecylate; Estradiol Valerate; Estrazinol Hydrobromide; Estriol; Estrofurate; Estrogens, Conjugated; Estrogens, Esterified; Estrone; Estropipate; Ethinyl Estradiol; Fenestrel; Mestranol; Nylestriol; and Quinestrol.

Fibrinolytic: Anistreplase; Bisobrin Lactate; and Brinolase.

Free oxygen radical scavenger: Pegorgotein.

Gastric Acid Suppressant: Lansoprazole, Pantoprazole and Omeprazole.

Gastrointestinal Motility agents: Cisapride.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate;

Carbenoxolone Sodium; Clocortolone Acetate; Clocortolone Pivalate; Cloprednol; Corticotropin; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; and Triamcinolone Hexacetonide.

Gonad-stimulating principle: Buserelin Acetate; Clomiphene Citrate; Ganirelix Acetate; Gonadorelin Acetate; Gonadorelin Hydrochloride; Gonadotropin, Chorionic; and Menotropins.

Hormone: 17 Alpha Dihydroequilenin; 17 Alpha Dihydroequilin; 17 Alpha Estradiol; 17 Beta Estradiol; 17 Hydroxy Progesterone; Androstenedione; Clomiphene; Cosyntropin; Dehydroepiandrosterone; Dihydroestosterone; Equilenin; Ethyndiol; Follicle Regulatory Protein; Follicle Stimulating Hormone; Folliculostatin; Gonadoctrinins; Gonadorelin; Gonadotropins; Han Memopausal Gonadotropins; Human Chorionic Gonadotropin; Insulin Growth Factor; Leuprolide; Levonorgestrel; Luteinizing hormone; Luteinizing Hormone Releasing Hormone and Analogs; Medroxyprogesterone; Megestrol; Metogest; Norethindrone; Norethynodrel; Norgestrel; Oocyte Maturation Inhibitor; Oxytocin; Pituitary, Posterior; Progesterone; Relaxin; Seractide Acetate; Somalapor; Somatrem; Somatropin; Somenopor; Somidobove; Tamoxifen; Urofollitropin; and Vasopressin.

Hypocholesterolemic: Lifibrol.

Hypoglycemic: Darglitazone Sodium; and Glimepiride.

Hypolipidemic: Azalanstat Dihydrochloride; Colestolone; Surfomer; and Xenalipin.

Hypotensive: Viprostol.

Immunizing agent: Antirabies Serum; Antivenin; Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; Rho(D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Vaccinia Immune Globulin; VaricellaZoster Immune Globulin; and Yellow Fever vaccine.

Immunomodulator: Dimepranol Acedoben; Imiquimod; Interferon Beta-1b; Lisofylline; Mycophenolate Mofetil; and Prezatide Copper Acetate.

Immunoregulator: Azarole; Fanetizole Mesylate; Frentizole; Oxamisole Hydrochloride; Ristianol Phosphate; Thymopentin; and Tilomisole.

Immunostimulant: Loxoribine; and Teceleukin.

Immunosuppressant: Azathioprine; Azathioprine Sodium; Cyclosporine; Daltroban; Gusperimus Trihydrochloride; Sirolimus; and Tacrolimus.

Impotence therapy adjunct: Delequamine Hydrochloride.

Inhibitor: Acarbose; Atorvastatin Calcium; Benserazide; Brocresine; Carbidopa; Clavulanate Potassium; Dazmegrel; Docebenone; Epoprostenol; Epoprostenol Sodium; Epristeride; Finasteride; Flurbiprofen Sodium; Furegrelate Sodium; Lufironil; Miglitol; Orlistat; Pimagedine Hydrochloride; Pirmagrel; Ponalrestat; Ridogrel; Sulbactam Benzathine; Sulbactam Pivoxil; Sulbactam Sodium; Suronacrine Maleate; Tazobactam; Tazobactam Sodium; Ticlopidine Hydrochloride; Tirilazad Mesylate; Tolrestat; Velnacrine Maleate; Zifrosilone; and Zileuton.

Keratolytic: Alcloxa; Aldioxa; Dibenzothiophene; Etaretene; Motretinide-I Picotrin Diolamine; Salicylic Acid; Sumarotene; Tazarotene; Tetroquinone; and Tretinoin.

LHRH agonist: Deslorelin; Goserelin; Histrelin; Lutrelin Acetate; and Nafarelin Acetate.

Liver disorder treatment: Malotilate.

Luteolysin: Fenprostalene.

Memory adjuvant: Dimoxamine Hydrochloride; and Ribaminol.

Mental performance enhancer: Aniracetam.

Mood regulator: Fengabine.

Mucolytic: Acetylcysteine; Carbocysteine; and Domiodol.

Mucosal Protective agents: Misoprostol (Cytotec).

Mydriatic: Berefrine.

Nasal decongestant: Nemazoline Hydrochloride; Pseudoephedrine Polistirex.

Neuroleptic: Duoperone Fumarate; and Risperidone.

Neuromuscular blocking agent: Atracurium Besylate; Cisatracurium Besylate; Doxacurium Chloride; Gallamine Triethiodide; Metocurine Iodide; Mivacurium Chloride; Pancuronium Bromide; Pipecuronium Bromide; Rocuronium Bromide; Succinylcholine Chloride; Tubocurarine Chloride; and Vecuronium Bromide.

Neuroprotective: Dizocilpine Maleate.

NMDA antagonist: Selfotel.

Non-hormonal sterol derivative: Pregnenolone Succinate.

Oxytocic: Carboprost; Carboprost Methyl; Carboprost Tromethamine; Dinoprost; Dinoprost Tromethamine; Dinoprostone; Ergonovine Maleate; Meteneprost; Methylergonovine Maleate; and Sparteine Sulfate.

Paget's disease agents: Tiludronate Disodium.

Progestin: Algestone Acetophenide; Amadinone Acetate; Anagestone Acetate; Chlormadinone Acetate; Cingestol; Clogestone Acetate; Clomegestone Acetate; Desogestrel; Dimethisterone; Dydrogesterone; Ethynerone; Ethynodiol Diacetate; Etonogestrel; Flurogestone Acetate; Gestaclone; Gestodene; Gestonorone Caproate; Gestrinone; Haloprogesterone; Hydroxyprogesterone Caproate; Lynestrenol; Medrogestone; Medroxyprogesterone Acetate; Methynodiol Diacetate; Norethindrone Acetate; Norgestimate; Norgestomet; Oxogestone Phenpropionate; Quingestanol Acetate; Quingestrone; and Tigestol.

Prostaglandin: Cloprostenol Sodium; Fluprostenol Sodium; Gemeprost; Prostalene; and Sulprostone.

Prostate growth inhibitor: Pentomone.

Prothyrotropin: Protirelin.

Psychotropic: Minaprine.

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine 1131; Tolpovidone 1131; Triolein 1125; and Triolein 1131.

Regulator: Calcifediol; Calcitonin; Calcitriol; Clodronic Acid; Dihydrotachysterol; Etidronic Acid; Oxidronic Acid; Piridronate Sodium; Risedronate Sodium; and Secalciferol.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalamide; Fenyripol Hydrochloride; Fetoxylate Hydrochloride; Flavoxate Hydrochloride; Fletazepam; Flumetramide; Hexafluorenium Bromide; Isomylamine Hydrochloride; Lorbamate; Mebeverine Hydrochloride; Mesuprine Hydrochloride; Metaxalone; Methixene Hydrochloride; Methocarbamol; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; and Xilobam.

Repartitioning agent: Cimaterol.

Scabicide: Amitraz; Crotamiton.

Sclerosing agent: Ethanolamine Oleate; Morrhuate Sodium; Tribenoside.

Sedative: Propiomazine.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam Ethchlorvynol; Etomidate; Fenobam; Flunitrazepam; Fosazepam; Glutethimide; Halazepam; Lonnetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Tracazolate; Trepipam Maleate; Triazolam; Tricetamide; Triclofos Sodium; Trimetozine; Uldazepam; Zaleplon; Zolazepam Hydrochloride; and Zolpidem Tartrate.

Selective adenosine A1 antagonist: Apaxifylline.

Serotonin antagonist: Altanserin Tartrate; Amesergide; Ketanserin; and Ritanserin.

Serotonin inhibitor: Cinanserin Hydrochloride; Fenclonine; Fonazine Mesylate; and Xylamidine Tosylate.

Serotonin receptor antagonist: Tropanserin Hydrochloride.

Steroid: Dexamethasone Acefurate; and Mometasone Furoate.

Stimulant: Amfonelic Acid; Amphetamine Sulfate; Ampyzine Sulfate; Arbutamine Hydrochloride; Azabon; Caffeine; Ceruletide; Ceruletide Diethylamine; Dazopride Fumarate; Dextroamphetamine; Dextroamphetamine Sulfate; Difluanine Hydrochloride; Dimefline Hydrochloride; Doxapram Hydrochloride; Ethamivan; Etryptamine Acetate; Fenethylline Hydrochloride; Flubanilate Hydrochloride; Flurothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; and Xamoterol Fumarate.

Suppressant: Amflutizole; Colchicine; Tazofelone.

Symptomatic multiple sclerosis: Fampridine.

Synergist: Proadifen Hydrochloride.

Thyroid hormone: Levothyroxine Sodium; Liothyronine Sodium; and Liotrix.

Thyroid inhibitor: Methimazole; and Propylthiouracil.

Thyromimetic: Thyromedan Hydrochloride.

Tranquilizer: Bromazepam; Buspirone Hydrochloride; Chlordiazepoxide; Clazolam; Clobazam; Clorazepate Dipotassium; Clorazepate Monopotassium; Demoxepam; Dexmedetomidine; Enciprazine Hydrochloride; Gepirone Hydrochloride; Hydroxyphenamate; Hydroxyzine Hydrochloride; Hydroxyzine Pamoate; Ketazolam; Lorazepam; Lorzafone; Loxapine; Loxapine Succinate; Medazepam Hydrochloride; Nabilone; Nisobamate; Oxazepam; Pentabamate; Pirenperone; Ripazepam; Rolipram; Sulazepam; Taciamine Hydrochloride; Temazepam; Triflubazam; Tybamate; and Valnoctamide.

Unstable angina agents: Tirofiban Hydrochloride.

Uricosuric: Benzbromarone; Irtemazole; Probenecid; Sulfinpyrazone.

Vasoconstrictor: Angiotensin Amide; Felypressin; Methysergide; and Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; and Xanthinol Niacinate.

Wound healing agent: Ersofermin.

Xanthine oxidase inhibitor: Allopurinol; and Oxypurinol.

Other active agents include: 16-Alpha Fluoroestradiol; 16Alpha-Gitoxin; 16-Eplestriol; 17 Alpha Estradiol; 17Beta Estradiol; 1Alpha-Hydroxyvitamin D2; 1-Decpyrrolidinone; 1-Dodecpyrrolidinone; 22-Oxacalcitriol; 2CVV; 2'-Nor-cGMP; 3-Isobutyl GABA; 6-FUDCA; 7-Methoxytacrine; Abacavir Sulfate; Abanoquil; Abecarnil; Acadesine; Acamprosate; Acebutolol Hydrochloride; Aceclofenac; Acetomepregenol; Acetrizoate Sodium; Acetylcysteine, N-;

Acetyldigitoxin; Acetyl-L-carnitine; Acetylmethadol; Acipimox; Acitemate; Aclatonium; Aconiazide; Acrivastinet; Adafenoxate; Adatanserin; Adefovir Dipivoxil; Adelmidrol; Ademetionine; Adiposin; Adrafinil; Alacepril; Aladapcin; Alaptide; Alatrofloxacin Mesylate; Albolabrin; Albumin Chromated Cr-51 Serum; Albumin Human; Albumin Iodinated I-125 Serum; Albumin Iodinated 1-131 Serum; Aldecalmycin; Alendronic Acid; Alentemol; Alfacalcidol; Alfuzosin; Alglucerase; Alinastine; Alitretinoin; Alkavervir; Allopurinol Sodium; Almotriptan Malate; Alosetron; Alpha Idosone; Alpha-Tocopherol; Alpha-Tocopherol Acetate; Alseroxylon; Altromycin B; Amantadine-HCl; Ambenonium Chloride; Amelometasone; Amezinium Metilsulfate; Amfebutamone; Amifloxacin; Aminolevulinic Acid Hydrochloride; Aminosalicylic Acid Resin Complex; Amiodarone Hydrochloride; Amisulpride; Amlodipine; Ammonium Lactate; Amphetamine Adipate; Amphetamine Aspartate; Amphetamine Resin Complex; Ampiroxicam; Amprenavir; Amylin; Amythiamicin; Ananain; Anaritide; Anileridine Phosphate; Anisindione; Anordrin; Apadoline; Apafant; Apraclonidine; Aprepitant; Aprosulate Sodium; Aprotinin Bovine; Aptiganel; Aranidipine; Arbekacin; Arbidol; Arbutamine; Arecatannin B 1; Argatroban; Aripiprazol; Aripiprazole; Arotinilol; Articaine Hydrochloride; Ascorbic Acid; Asimadoline; Aspalatone; Asperfuran; Aspoxicillin; Atazanavir Sulfate; Atenolol, S-; Atevirdine; Atomoxetine Hydrochloride; Atpenin B; Atrinositol; Aureobasidin A; Avobenzone; Azadirachtine; Azelaic Acid; Azelastine; Azelnidipine; Azimilide; Azithromycin Dihydrate; Aztreonwn; Baccatin III; Bacoside A; Bacoside B; Bactobolamine; Balazipone; Balhimycin; Balofloxacin; Balsalazide; Bambuterol; Baohuoside 1; Barnidipine; Batebulast; Beauvericin; Becaplermin; Becliconazole; Beclomethasone Dipropionate Monohydrate; Befloxatone; Bellenamine; Benflumetol; Benidipine; Bentoquatam; Benzisoxazole; Benzoidazoxan; Benzoyl Peroxide; Benzphetamine Hydrochloride; Benzquinamide Hydrochloride; Benztropine; Benzyl Benzoate; Benzyl Penicilloyl-Polylysine; Bepridil; Beractant; Beraprost; Berlafenone; Bertosamil; Besipirdine; Beta-Carotene; Betaine, Anhydrous; Betamipron; Betaxolol; Betazole Hydrochloride; Bevantolol; Bexarotene; Bifemelane; Bimakalim; Bimatoprost; Bimithil; Binospirone; Biotin; Bioxalomycin Alpha2; Biriperone; Bisaramil; Bisaziridinylspermine; Bis-Benzimidazole A; Bis-Benzimidazole B; Bismuth Subsalicylate; Bistramide D; Bistramide K; Boldine; Bopindolol; Bortezomib; Brefeldin; Brimonidine; Brinzolamide; Bromfenac; Bucindolol; Budipine; Bunazosin; Butenafine; Butenafine Hydrochloride; Butixocort Propionate; Cabergoline; Caffeine Citrate; Calanolide A; Calcitonin Human; Calcitonin, Salmon; Calcium; Calcium Acetate; Calcium Gluceptate; Calcium Metrizoate; Calfactant; Camonagrel; Candesartan; Candesartan Cilexetil; Candoxatrilat; Capromab; Capsaicin; Carbamazepine; Carbazomycin C; Carbetocin; Carbidopa/Levodopa; Carbovir; Carboxymethylated Beta-1,3-Glucan; Carperitide; Carteolol; Carumonam; Carvotroline; Caspofungin Acetate; Cebaracetam; Cefadroxil; Cefadroxil Hemihydrate; Cefcapene Pivoxil; Cefdaloxime Pentexil Tosilate; Cefditoren Pivoxil; Cefepime Hydrochloride (Arginine Formulation); Cefetamet; Cefetamet Pivoxil; Cefffietazole; Cefluprenam; Cefminox; Cefodizime; Cefoselis; Cefotiam; Cefotiam Hexetil; Cefozopran; Cefpirome; Cefsulodin; Ceftazidime (Arginine Formulation); Ceftazidime Sodium; Cefteram; Ceftibuten Dihydrate; Ceftriaxone; Celastrol; Celecoxib; Celikalim; Celiprolol; Cellulose Sodium Phosphate; Cepacidine A; Cericlamine; Cerivastatin; Cerivastatin Sodium; Certoparin Sodium; Cetiedil; Cetirizine; Cetyl Alcohol; Cevimeline Hydrochloride; Chlormerodrin, Hg-197; Chlormezanone; Chloroorienticin A; Chloroorienticin B; Cholecalciferol; Cholestyramine; Choriogonadotropin Alfa; Chromic Phosphate, P-32; Chymopapain; Chymotrypsin; Cibenzoline; Ciclesonide; Cicloprolol; Cilansetron; Cilnidipine; Cilobradine; Cilostazol; Cimetropiurn Bromide; Cinitapride; Cinolazepam; Ciprostene; Cisapride Monohydrate; Cisatracurium, Besilate; Cistinexine; Citalopram; Citalopram Hydrobromide; Citicoline; Citreamicin Alpha; Clausenamide; Clidinium Bromide; Clinafloxacin; Clomethiazole; Clopidogrel; Clopidogrel Bisulfate; Cobalt Chloride, Co-57; Cobalt Chloride, Co-60; Colesevelam Hydrochloride; Colestimide; Colfosceril Palmitate; Complestatin; Contignasterol; Contortrostatin; Corticotropin Zinc Hydroxide; Cosalane; Costatolide; Cotinine; Cournermycin AI; Cryptenamine Acetates; Cryptenamine Tannates; Cucumariosid; Curdlan Sulfate; Curiosin; Cyanocobalamin; Cyanocobalamin, Co-57; Cyanocobalamin, Co-58; Cyanocobalamin, Co-60; Cyclazosin; Cyclic HPMPC; Cyclobenzaprine; Cyclobut A; Cyclobut G; Cyclocapron; Cyclosin; Cyclothialidine; Cyclothiazomycin; Cycrimine Hydrochloride; Cyproterone; Cysteamine Bitartrate; Cytochalasin B; Dactimicin; Daidzein; Daidzin; Danaparoid; Daphnodorin A; Dapiprazole; Dapitant; Darifenacin; Darlucin A; Darsidomine; Daunorubicin Citrate; DdUTP; Decamethonium Bromide; Deferiprone; Deferoxamine Mesylate; Dehydrodidemnin B; Delapril; Delequarnine; Delfaprazine; Delmopinol; Delphinidin; Deoxypyridinoline; Deprodone; Depsidomycinderamciclane; Dermatan Sulfate; Deserpidine; Desirudin; Desloratadine; Desmopressin; Desoxoamiodarone; Desoxyribonuclease; Detajrniurn Bitartrate; Dexketoprofen; Dexloxiglumide; Dexmethylphenidate Hydrochloride; Dexrazoxane Hydrochloride; Dexsotalol; Dextrin 2-Sulphate; Dextroamphetamine Adipate; Dextroamphetamine Resin Complex; Dextroamphetamine Saccharate; Dextrose; Diclofenac Digolil; Dicranin; Dienogest; Diethylhomospennine; Diethylnorspermine; Difenoxin Hydrochloride; Dihydrexidine; Diltiazeim; Dimethyl Prostaglandin A1; Dimethylhomospermine; Dimiracetarn; Dimyristoyl Lecithin; Diphemanil Methylsulfate; Diphencyprone; Diphenylpyraline Hydrochloride; Diprafenone; Dipropylnorspermine; Discodermolide; Divalproex; Docarparnine; Docosanol, 1-; Dolasetron Mesylate Monohydrate; Domitroban; Donepezil Hydrochloride; Dorzolamide; Dosmalfate; Dotarizine; Doxazosin; Doxercalciferol; Draculin; Drosperidone; Drospirenone; Drotaverine Acephyllinate; Droxicam; Dutasteride; Ebiratide; Ebrotidine; Ecabapide; Ecabet; Ecdisteron; Echicetin; Echistatin; Ecteinascidin 722; Ecteinascidin 729; Ecteinascidin 743; Edaravone; Edetate Calcium Disodium; Edetate Disodium; Edobacomab; Edrecolornab; Efavirenz; Efegatran; Efonidipine; Egualen; Elcatonin; Eletriptan; Eletriptan Hydrobromide; Elgodipine; Eliprodil; Eltenac; Emakalim; Emedastine; Emedastine Difumarate; Emiglitate; Emoctakin; Emtricitabine; Enalapril; Enazadrem; Enfuvirtide; Englitazone; Entacapone; Entero statin; Eplerenone; Epoxymexrenone; Eptastigmine; Eptifibatide; Erdosteine; Ergocalciferol; Ersentilide; Ertapenem Sodium; Erythritol; Escitalopram Oxalate; Esomeprazole Magnesium; Estazolam; Estradiol Acetate; Esuprone; Etanterol; Ethacizin; Ethchlorvynol; Ethinamate; Ethinylestradiol; Ethoxzolamide; Etidocaine Hydrochloride; Etizolam; Etrabamine; Eveminomicin; Examorelin; Ezetimibe; Faerieftmgin; Fantofarone; Farnciclovir; Faropenem; Fasidotril; Fasudil; Fedotozine; Felbarnate; Fenofibrate; Fenoldopam; Fenspiride; Fentanyl; Fenticonazole; Fepradinol; Ferpifosate Sodium; Ferristene; Ferrixan; Ferrous Citrate, Fe-59; Fexofenadine Hydrochloride; Fibrinogen, 1-125; Fibrinolysin; Flecainide; Flerobuterol; Flesinoxan; Flezelastine; Flobufen; Flomoxef; Florfenicol; Florifenine; Flornastat; Flosatidil; Fludeoxyglucose, F-18; Flumecinol; Flunarizine; Fluocalcitriol; Fluoxetine, R-; Fluoxetine, S-; Fluparoxan; Flupirtine; Flurbiprofen Axetil; Flurithromycin; Flutamide; Flutrimazole; Fluvastatin; Fluvoxamine; Folic Acid; Follitropin Alfa; Follitropin Alfa/Beta; Fomivirsen Sodium; Fondaparinux Sodium; Forasartan; Formoterol; Formoterol Fumarate; Formoterol, R,R; Fosinopril; Fosphenytoin; Frovatriptan Succinate; Fulvestrant; Furosernide; Gadobenic Acid; Gadobutrol; Gadodiamide-EOB-DTPA; Gadopentetate Dimeglumine; Gadoteric Acid; Galantamine; Galantamine Hydrobromide; Galdansetron; Gallopamil; Gamolenic Acid; Gatifloxacin; Gefitinib; Gemifloxacin Mesylate; Gemtuzumab Ozogamicin; Gepirone; Girisopam; Glaspimod; Glatiramer Acetate; Glaucocalyxin A; Glucagon Hydrochloride; Glucagon Hydrochloride Recombinant; Glucagon Recombinant; Gluconolactone; Glutapyrone; Glutathione Disulfide; Glycopine; Glycopril; Goserelin Acetate; Grepafloxacin; Grepafloxacin Hydrochloride; Guaifenesin; Guanidine Hydrochloride; Halichondrin B; Halofantrine; Halomon; Haloperidol Lactate; Halopredone; Hatomarubigin C; Hatornambigin D; Hatornamicin; Hatornarubigin A; Hatornarubigin B; Heparin Calcium; Heparin Sodium; Hexocyclium Methylsulfate; Hexylcaine Hydrochloride; Histrelin Acetate; Hyaluronidase; Hydrocortamate Hydrochloride; Hydrocortisone Cypionate; Hydrocortisone Probutate; Hydroquinone; Hydroxocobalamin; Hydroxypropyl Cellulose; Hydroxystilbamidine Isethionate; Ibandronate Sodium; Ibogaine; Ibudilast; Ibuprofen Potassium; Icodextrin; Illimaquinone; Iloprost; Imatinib Mesylate; Imidapril; Imidazenil; Imiglucerase; Imipramine Pamoate; Inamrinone Lactate; Indapamide; Indinavir; Indinavir Sulfate; Indium In-Ill Oxyquinoline; Indium In-Ill Pentetate Disodium; Indium In-Ill Pentetreotide Kit; Indometacin; Indometacin Farnesil; Indomethacin Sodium; Inocoterone; Inogatran; Inolimomab; Insulin Aspart; Insulin Aspart Protamine; Insulin Glargine; Insulin Lispro Protamine; Interferon Alfa; Interferon Alfa-NI; Interferon Beta; Interferon Beta-lal; Interferon Gamma-I A; Interferon Gamma-I B; Interferon Omega; Interferon, Consensus; interleukin-3; Interleukin-1; Interleukin-I Beta; Interleukin-10; Interleukin-11; Interleukin-12; Interleukin-15; Interleukin-2; Interleukin-4; Interleukin-5; Interleukin-7; Interleukin-8; Interleukinl Alpha; Intrinsic Factor; Inulin; Invert Sugar; Iobenguane Sulfate I 131; Iobitridol; Iodamide Meglumine; Iodipamide Sodium; Iodoamiloride; Iodohippurate Sodium, 1-123; Iodohippurate Sodium, 1-131; Iofetamine Hydrochloride 1-123; Iofratol; Iopromide; Iopyrol; Iorneprol; Iothalamate Sodium, 1-125; Iotriside; Ioxaglate Sodium; Ipazilide; Ipenoxazone; Ipidacrine; Ipomeanol, 4; Ipriflavone; Ipsapirone; Irbesartan; Irloxacin; Iron Dextran; Iron Sucrose; Irternazole; Isalsteine; Isbogrel; Iseparnicin; Isofloxythepin; Isopropyl Unoprostone; Itameline; Itopride; Ketoprofen, R-; Ketoprofen, S-; Ketorolac; Lactitol; Lactivicin; Lactulose; Laennec; Lafutidine; Lanoconazole; Lanperisone; Larnifiban; Larnotrigine; Latanoprost; Lateritin; Laurocaprarn; Leflunomide; Lemefloxacin; Leminoprazole; Lenercept; Lepirudin; Leptin; Lercanidipine; Lerisetron; Lernildipine; Lesopitron; Letrazuril; Leucomyzin; Levalbuterol Hydrochloride; Levallorphan Tartrate; Levamisole Hydrochloride; Levetiracetam; Levobetaxolol; Levobunolol; Levobupivacaine; Levobupivacaine Hydrochloride; Levocabastine; Levocarnitine; Levodropropizine; Levofloxacin; Levopropoxyphene Napsylate, Anhydrous; Levormeloxifene; Levornoprolol; Levosimendan; Levosulpiride; Lindane; Linezolid; Linotroban; Linsidornine; Lintitript; Lintopride; Lipase; Lirexapride; Lithium Carbonate; Lithium Citrate; Lodoxamide; Lomerizine; Lonazolac; Lopinavir; Lorglumide; Losartan; Losigamone; Loteprednol; Loviride; Loxapine Hydrochloride; LpdR; Lubeluzole; Lutetium; Luzindole; Lydicamycin; Lysostaphin; Magainin 2 Arnide; Magnesium Acetate; Magnesium Acetate Tetrahydrate; Magnolol; Malathion; Mallotochromene; Mallotojaponin; Mangafodipir; Mangafodipir Trisodium; Manidipine; Maniwamycin A; Mannitol; Manurnycin E; Manurnycin F; Mapinastine; Martek 8708; Martek 92211; Massetolide; Meglumine Metrizoate; Meloxicam; Melphalan Hydrochloride; Menadiol Sodium Diphosphate; Menadione; Meprednisone; Mequinol; Mersalyl Sodium; Mesna; Metformin Hydrochloride; Methantheline Bromide; Metharbital; Methoxamine Hydrochloride; Methoxatone; Methoxsalen; Methscopolamine Bromide; Methyclothiazide; Methyldopa; Methylhistamine, R-alpha; Methylinosine Monophosphate; Methylprednisolone Aceponate; Methyprylon; Metiparnide; Metipranolol Hydrochloride; Metolazone; Metoprolol Fumarate; Metoprolol, S-; Metoprotol Tartrate; Metrifonate; Metrizoate Magnesium; Metrizoic Acid; Mezlocillin Sodium Monohydrate; Michellarnine B; Microcolin A; Midodrine; Miglustat; Milacernide; Milarneline; Mildronate; Milnacipran; Milrinone Lactate; Miokarnycin; Mipragoside; Mirfentanil; Mivazerol; Mixanpril; Mizolastine; Mizoribine; Moexipril; Moexipril Hydrochloride; Mofezolac; Mometasone; Mometasone Furoate Monohydrate; Monobenzone; Montirelin; Moracizine; Moricizine Hydrochloride; Mosapramine; Mosapride; Motilide; Moxifloxacin Hydrochloride; Moxiraprine; Moxonidine; Mupirocin; Mupirocin Calcium; Mycophenolate Mofetil Hydrochloride; Nadifloxacin; Nadroparin Calcium; Nafadotride; Nafamostat; Naftopidil; Naglivan; Nalmefene Hydrochloride; Naltrexone Hydrochloride; Napadisilate; Napsagatran; Naratriptan; Nasaruplase; Nateglinide; Nateplasel; Nelfinavir Mesylate; Nesiritide; Niacinamide; Nicotine; Nicotine Polacrilex; Niperotidine; Niravoline; Nisin; Nitazoxanide; Nitecapone; Nitisinone; Nitrendipine, S-; Nitrofurantoin Monohydrate; Nitrofurantoin Sodium; Nitrofurantoin, Macrocrystalline; Nitrofurazone; Nitroglycerin; Nonoxynol-9; Norelgestromin; Octyl Methoxycinnamate; Olmesartan Medoxomil; Olopatadine; Olopatadine Hydrochloride; Olprinone; Olsalazine; Omeprazole Magnesium; Ondansetron, R-; Oral Hypoglyceremics; Orphenadrine Hydrochloride; Oseltamivir Phosphate; Otenzepad; Oxamisole; Oxaprozin Potassium; Oxcarbazepine; Oxiconazole; Oxiracetam; Oxodipine; Oxybenzone; Oxybutynin; Oxyphencyclimine Hydrochloride; Oxyphenonium Bromide; Ozagrel; Palauarnine; Palinavir; Palonosetron Hydrochloride; Pamaparin Sodium; Panamesine; Pancrelipase; Panipenem; Panipenum; Pannorin; Panornifene; Pantethine; Pantoprazole Sodium; Pantothenic Acid; Paramethadione; Paricalcitol; Parnaqueside; Parnicogrel; Paroxetine Hydrochloride; Paroxetine Mesylate; Parthenolide; Pazufloxacin; Pegademase Bovine; Pegvisomant; Pemirolast; Pemirolast Potassium; Penciclovir Sodium; Penicillamine; Pentafuside; Pentagastrin; Pentamidine; Pentamidine Isethionate; Pentetate Calcium Trisodium Yb-169; Pentigetide; Pentolinium Tartrate; Pentosan; Perflexane; Perfluoropolymethylisopropyl Ether; Perflutren; Pergolide; Pergolide Mesylate; Perindoprilat; Pernedolac; Perospirone; Phenaridine; Phenindione; Pheniramine Maleate; Phenmetrazine Hydrochloride; Phenotoxifvline; Phenserine; Phensuccinal; Phentermine Resin Complex; Phentolamine Mesilate; Phenylalanyl Ketoconazole; Phenylephrine Bitartrate; Phenytoin Sodium, Extended; Phenytoin Sodium, Prompt; Phosphoric Acid; Phytonadione; Picenadol; Picroliv;

Picumeterol; Pidotimod; Pilsicainide; Pimagedine; Pimecrolimus; Pimilprost; Pinocebrin; Pioglitazone; Piperonyl Butoxide; Pirlindole; Pirmenol; Pirodomast; Polyestradiol Phosphate; Polyethylene Glycol 3350; Polytetrafluoroethylene; Poractant Alfa; Potassium Chloride; Pramipexole Dihydrochloride; Praziquantel; Prazosin; Prilocaine; Procaine Merethoxylline; Proguanil Hydrochloride; Propagermanium; Propentofylline; Propiolactone; Propiomazine Hydrochloride; Propionylcamitine, L-; Propiram; Propiram+Paracetamol; Propiverine; Prostratin; Protegrin; Protein Hydrolysate; Protokylol Hydrochloride; Protosufloxacin; Prulifloxacin; Pyrethrins; Pyridoxine; Pyridoxine Hydrochloride; Quazeparn; Quetiapine; Quetiapine Fumarate; Quiflapon; Quinagolide; Quinapril; Quinethazone; Quinidine Polygalacturonate; Raloxifene; Ramatroban; Ranelic Acid; Ranolazine; Rapacuronium Bromide; Recainarn; Regavirumab; Repaglinide; Rescinnamine; Resinferatoxin; Reticulon; Reviparin Sodium; Revizinone; Riboflavin; Riboflavin Phosphate Sodium; Ricasetron; Rilopirox; Rimantadine; Rimexolone; Rimoprogin; Riodipine; Ripisartan; Risedronic Acid; Rispenzepine; Ritipenem Acoxil; Ritipenem; Ritonavir; Rivastigmine Tartrate; Rizatriptan Benzoate; Rnibefradil; Rnivacurium Chloride; Rofecoxib; Rokitamycin; Ropinirole; Ropivacaine; Ropivacaine Hydrochloride Monohydrate; Roquinirnex; Rose Bengal Sodium, 1131; Rosiglitazone Maleate; Roxatidine; Roxindole; Rubidium Chloride Rb-82; Rufloxacin; Rupatidine; Ruzadolane; Sacrosidase; Safflower Oil; Safironil; Salbutarnol, R-; Salnacedin, R-; Samarium Sm 153 Lexidronam Pentasodium; Sanfetrinem; Saprisartan; Sapropterin; Saquinavir; Sarcophytol A Sargramostim; Sarneridine; Sarnpatrilat; Sarpogrelate; Saruplase; Saterinone; Satigrel; Satumomab Pendetide; Scopolamine; Secretin; Selenomethionine, Se-75; Sematilide; Sermorelin; Sernotiadil; Sertaconazole; Sertraline; Sertraline-HCl; Setiptiline; Sevelamer Hydrochloride; Sevirurnab; Sezolamide; Sildenafil Citrate; Silipide; Silteplase; Silver Sulfadiazine; Simendan; Simethicone; Simethicone-Cellulose; Sinitrodil; Sinnabidol; Sipatrigine; Sirnvastatin; Somatomedin C; Somatropin Recombinant; Sorbitol; Sornatomedin B; Somatrem; Somatropin; Sotalol; Staurosporine; Stepronin; Stobadine; Strontium Chloride, Sr-89; Succibun; Sulfanilamide; Sulfaphenazole; Sulfapyridine; Sulfoxamine; Sulfoxone Sodium; Sulfur; Sultamicillin; Sultopride; Sumatriptan; Sutilains; Symakalim; Talbutal; Tandospirone; Tannic Acid; Tapgen; Taprostene; Tartaric Acid; Tazanolast; Tegaserod Maleate; Telenzepine; Telmesteine; Telmisartan; Temocapril; Tenofovir Disoproxil Fumarate; Tenosal; Tepirindole; Terazosin; Terbinafine Hydrochloride; Terflavoxate; Terguride; Terlipressin; Terodiline; Tertatolol; Testosterone Buciclate; Thallous Chloride, Tl-201; Thiamine; Thiamine Hydrochloride; Thiofedrine; Thiomarinol; Thioperamide; Thiosemicarbazone; Thonzonium Bromide; Thyroglobulin; Thyrotropin; Thyrotropin Alfa; Tiagabine; Tiagabine Hydrochloride; Tianeptine; Tiapafant; Ticlopidine; Tienoxolol; Tilisolol; Tilnoprofen Arbamel; Tiludronic Acid; Tiopronin; Tiotropium Bromide; Tirandalydigin; Tirilazad; Tirofiban; Tiropramide; Tocopherol Acetate; Tolterodine Tartrate; Torasemide; Trafennin; Trandolapril; Tranylcypromine Sulfate; Travoprost; Traxanox; Trazodone-HCl; Treprostinil Sodium; Tretinoin Tocoferil; Triarntevene; Tricaprilin; Trichohyalin; Trichosanthin, Alpha; Triclosan; Tridihexethyl Chloride; Trientine; Trientine Hydrochloride; Triflavin; Trimegestone; Trimethoprim Hydrochloride; Trioxsalen; Triptorelin Pamoate; Trolamine Polypeptide Oleate Condensate; Trombodipine; Trometarnol; Tromethamine; Tropine Ester; Trospectomycin; Trovafloxacin; Trovafloxacin Mesylate; Trovirdine; Tucaresol; Tulobuterol; Tylogenin; Tyloxapol; Undecoylium Chloride; Undecoylium Chloride Iodine Complex; Unoprostone Isopropyl; Urapidil; Urea, C-13; Urea, C-14; Uridine Triphosphate; Valaciclovir; Valdecoxib; Valganciclovir Hydrochloride; Valproate Magnesium; Valproate Semisodium; Valrubicin; Valsartan; Vamicamide; Vanadeine; Vaninolol; Vasopressin Tannate; Venlafaxine; Verapamil, (S); Veratrum Viride; Veroxan; Vexibinol; Vinburnine Citrate; Vinburnine Resinate; Vinconate; Vinpocetine; Vinpocetine Citrate; Vintoperol; Viomycin Sulfate; Vitamin A; Vitamin A Palmitate; Vitamin E; Vitamin K; Voriconazole; Voxergolide; Warfarin Potassium; Xemilofiban; Ximoprofen; Yangarnbin; Zabicipril; Zacopride; Zacopride, R-; Zafirlukast; Zalospirone; Zaltoprofen; Zanamivir; Zanarnivir; Zankiren; Zatebradine; Zatosetron; Zenarestat; Zinostatin Stimalarner; Ziprasidone; Ziprasidone Mesylate; Zoledronic Acid; Zolmitriptan; Zolpidem; Zopiclone; Zopiclone, S-; Zopolrestat; and Zotepine. Still other examples of therapeutically active agents are listed in 2000 MedAd News 19:56-60 and The Physicians Desk Reference, 53rd. Edition, pages 792-796, Medical Economics Company (1999).

Embodiments of the present disclosure will be described with reference to the following Examples which are provided for illustrative purposes only and should not be used to limit the scope of or construe the invention.

EXAMPLES

Example 1

Transdermal/Topical Delivery Formulations

Several formulations were prepared according to embodiments of the present disclosure utilizing the compositional components set forth in Tables 1A and 1B. Each of the formulations was prepared in a batch at a batch size of 2 kg. All raw materials were stored at ambient conditions prior to manufacturing of the formulations. Generally, all formulations were manufactured as described below.

The organic phase, containing isopropyl alcohol, di-isopropyl adipate, hexylene glycol, halobetasol propionate was added into an aqueous phase containing purified water, anhydrous citric acid, di-hydrate sodium citrate, and if present in the formulation SLSA. This mixture was then combined with any other MMPE™s found in the formulation and if present in the formulation polyoxyl 35 castor oil. A bench top mixer was used to ensure complete dissolution after each component addition. The order of ingredients combined may vary depending on the preparation of laboratory vs. GMP batches.

TABLE 1A

Example Formulations Control and F1-F6 (wt %)

| Ingredient | C1 Control | F1 | F2 | F3 | F4 | F5 | F6 |
|---|---|---|---|---|---|---|---|
| Halobetasol Propionate | 0.05 | 0.05 | 0.05 | 0.05 | 0.05 | 0.05 | 0.05 |
| Isopropyl Alcohol (IPA) | 35.0 | 35.0 | 35.0 | 35.0 | 35.0 | 35.0 | 35.0 |
| Di-Isopropyl Adipate (DIA) | 3.0 | 3.0 | 3.0 | 3.0 | 3.0 | 3.0 | 3.0 |
| Hexylene Glycol | 7.5 | 7.5 | 7.5 | 7.5 | 7.5 | 7.5 | 7.5 |

TABLE 1A-continued

Example Formulations Control and F1-F6 (wt %)

| Ingredient | C1 Control | F1 | F2 | F3 | F4 | F5 | F6 |
|---|---|---|---|---|---|---|---|
| Citric Acid, anhydrous | 0.09 | 0.09 | 0.09 | 0.09 | 0.09 | 0.09 | 0.09 |
| Sodium Citrate, dihydrate | 0.07 | 0.07 | 0.07 | 0.07 | 0.07 | 0.07 | 0.07 |
| Purified Water | 54.29 | 47.79 | 47.79 | 47.79 | 52.79 | 47.29 | 47.29 |
| Polyoxyl 35 Castor Oil | — | 5.0 | 5.0 | 5.0 | 0 | 5.0 | 5.0 |
| Methyl Laurate (ML) | — | 0.5 | 0.5 | 0.5 | 0.5 | — | — |
| Isopropyl Myristate (IM) | — | 1.0 | — | — | — | 1.0 | 1.0 |
| Oleic Acid (OA) | — | — | 1.0 | — | — | 1.0 | — |
| Glyceryl Oleate (GO) | — | — | — | 1.0 | — | — | 1.0 |
| Sodium Lauryl Sulfoacetate (SLSA) | — | — | — | — | 1.0 | — | — |

TABLE 1B

Example Formulations F7-F11 (wt %)

| Ingredient | F7 | F8 | F9 | F10 | F11 |
|---|---|---|---|---|---|
| Halobetasol Propionate | 0.05 | 0.05 | 0.05 | 0.05 | 0.05 |
| Isopropyl Alcohol (IPA) | 35.0 | 35.0 | 35.0 | 35.0 | 35.0 |
| Di-Isopropyl Adipate (DIA) | 3.0 | 3.0 | 3.0 | 3.0 | 3.0 |
| Hexylene Glycol | 7.5 | 7.5 | 7.5 | 7.5 | 7.5 |
| Citric Acid, anhydrous | 0.09 | 0.09 | 0.09 | 0.09 | 0.09 |
| Sodium Citrate, dihydrate | 0.07 | 0.07 | 0.07 | 0.07 | 0.07 |
| Purified Water | 47.29 | 47.29 | 47.29 | 47.29 | 47.79 |
| Polyoxyl 35 Castor Oil | 5.0 | 5.0 | 5.0 | 5.0 | 5.0 |
| Methyl Laurate (ML) | — | — | — | — | 0.5 |
| Isopropyl Myristate (IM) | 1.0 | — | — | — | — |
| Oleic Acid (OA) | — | 1.0 | 1.0 | — | — |
| Glyceryl Oleate (GO) | — | 1.0 | — | 1.0 | — |
| Sodium Lauryl Sulfoacetate (SLSA) | 1.0 | — | 1.0 | 1.0 | 1.0 |

Example 2

Physical Stability of the Formulations of Example 1

Each of the formulations and the control described in Example 1 were stored at ambient conditions (25° C.). The physical stability (i.e. the phase separation of the formulations) of each of the formulations was tested at weeks one, two, three, four, eight, and twelve. The phase separation was measured by placing each of the formulations in a 10 ml graduated glass container. The cylinders were stopped and the phase separation was measured in terms of millimeters at the indicated time intervals. The containers were not moved during the course of this study.

The phase separation for each of the formulations is provided in Table 2. None of the formulations experienced any visible phase separation during the testing period.

TABLE 2

| | Phase Separation (ml) | | | | | | | | | | | |
|---|---|---|---|---|---|---|---|---|---|---|---|---|
| Week | C1 Control | F1 | F2 | F3 | F4 | F5 | F6 | F7 | F8 | F9 | F10 | F11 |
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 |

Example 3 pH of the Formulations of Example 1

Each of the formulations and the control described in Example 1 were stored at ambient conditions (25° C.). The pH of each of the formulations was tested following U.S. Pharmacopeial Convention (USP) procedure 791 as of the date of the present patent application filing. The pH of each of the formulations was tested at zero, four, eight, and twelve weeks. The pH for each of the formulations are provided in Table 3 and graphed in FIG. 1. All test formulations (F1 to F11) showed improved pH stability over the control formulation following 12 weeks of storage. The improvement in pH stability over the control formulation may become more pronounced for the test formulations at extended time intervals e.g. 6 months, 12 months, 24 months.

TABLE 3

| | pH | | | | | | | | | | | |
|---|---|---|---|---|---|---|---|---|---|---|---|---|
| Week | C1 Control | F1 | F2 | F3 | F4 | F5 | F6 | F7 | F8 | F9 | F10 | F11 |
| 0 | 4.74 | 4.98 | 4.86 | 5.07 | 4.78 | 4.91 | 5.07 | 4.90 | 4.92 | 4.84 | 4.93 | 4.92 |
| 4 | 4.75 | 4.95 | 4.91 | 5.09 | 4.79 | 4.91 | 5.06 | 4.91 | 4.95 | 4.83 | 4.92 | 4.90 |
| 8 | 4.73 | 5.02 | 4.90 | 5.07 | 4.79 | 4.93 | 5.07 | 4.89 | 4.95 | 4.84 | 4.93 | 4.90 |
| 12 | 4.80 | 5.02 | 4.91 | 5.06 | 4.79 | 4.90 | 5.07 | 4.88 | 4.95 | 4.83 | 4.94 | 4.90 |
| Total Change* | 0.06 | 0.04 | 0.05 | 0.01 | 0.01 | 0.01 | 0 | 0.02 | 0.03 | 0.01 | 0.01 | 0.02 |

*Calculated as change in pH between 0-week timepoint and 12-week timepoint.

Example 4

Viscosity of the Formulations of Example 1

Each of the formulations and the control described in Example 1 were stored at ambient conditions (25° C.). The viscosity of each of the formulations was tested following U.S. Pharmacopeial Convention (USP) procedure 911 as of the date of the present patent application filing. The viscosity of each of the formulations was tested at zero, four, eight, and twelve weeks. The viscosity for each of the formulations is provided in Table 4.

TABLE 4

| | | | | | viscosity (cps) | | | | | | | |
|---|---|---|---|---|---|---|---|---|---|---|---|---|
| Week | C1 Control | F1 | F2 | F3 | F4 | F5 | F6 | F7 | F8 | F9 | F10 | F11 |
| 0 | 4.11 | 5.61 | 5.49 | 5.94 | 4.26 | 6.51 | 6.21 | 5.94 | 5.94 | 5.76 | 5.76 | 5.46 |
| 4 | 3.96 | 5.64 | 5.76 | 5.82 | 3.99 | 5.61 | 5.58 | 5.28 | 5.85 | 5.61 | 5.70 | 5.55 |
| 8 | 3.90 | 5.64 | 6.39 | 5.67 | 3.69 | 6.39 | 5.70 | 5.64 | 5.94 | 5.28 | 5.73 | 5.34 |
| 12 | 3.72 | 5.13 | 5.04 | 5.19 | 3.57 | 5.91 | 5.79 | 5.55 | 5.64 | 5.34 | 5.64 | 5.31 |
| Total Change* | 0.39 | 0.48 | 0.45 | 0.75 | 0.69 | 0.60 | 0.42 | 0.39 | 0.30 | 0.42 | 0.12 | 0.15 |

*Calculated as change in cps between 0-week timepoint and 12-week timepoint.

Figure 2:
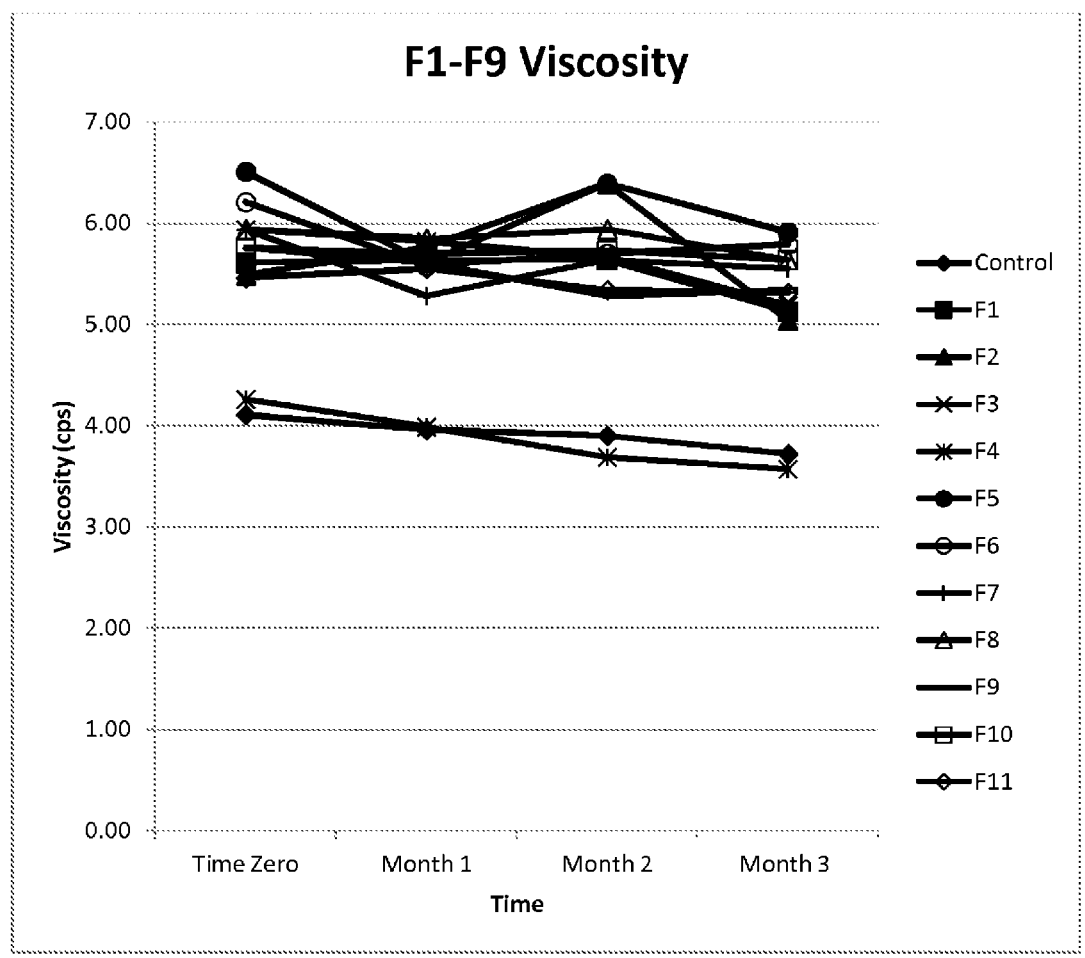
FIG. 2 is a plot of the viscosity of several exemplary embodiments of formulations disclosed herein.

The viscosity at 25° C. for each of the formulations is plotted and shown in FIG. 2. Formulations F8, F10 and F11 showed improved consistency of viscosity over the control formulation following 12 weeks of storage. The consistency of viscosity over the control formulation may become more pronounced for certain test formulations at extended periods of time, e.g. 6 months, 12 months, 24 months.

Example 5

Active Pharmaceutical Ingredient Assay of the Formulations of Example 1

Each of the formulations and the control described in Example 1 were stored at ambient conditions (25° C.). An active pharmaceutical ingredient (API) assay for each of the formulations was tested using High Performance Liquid Chromatography (HPLC) equipped with a Synergi™ Hydro-RP (4 μm, 100×3.0 mm) column. The API of each of the formulations was tested at zero, four, eight, and twelve weeks. The API assay results for each of the formulations are provided in Table 5.

Figure 3:
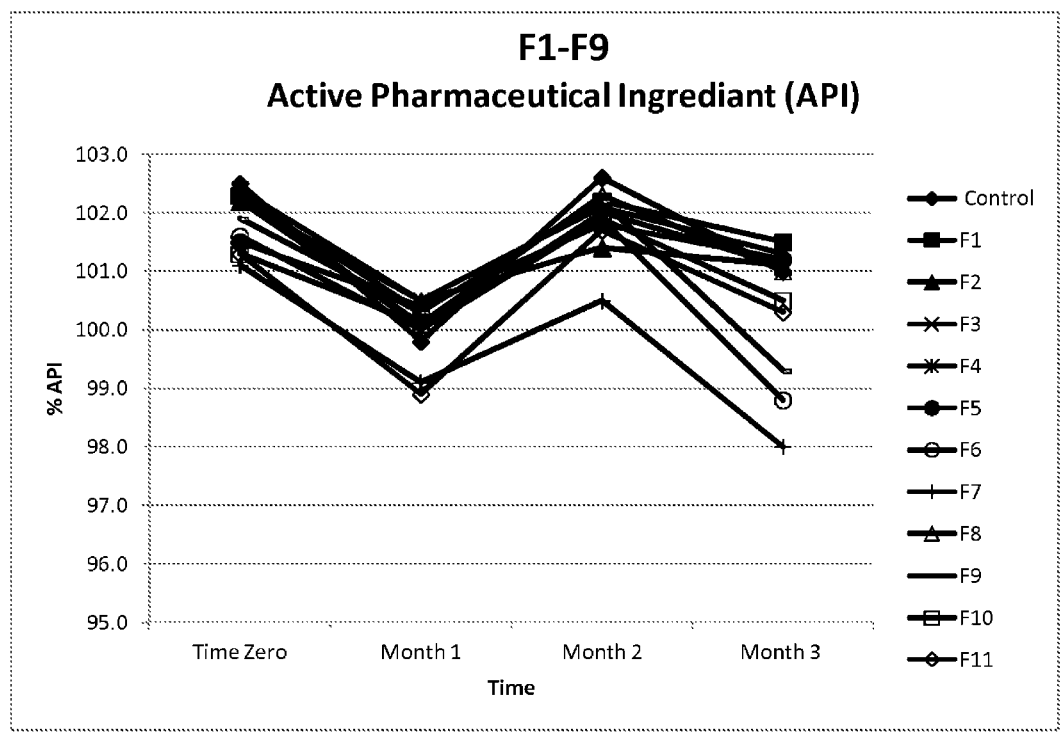
FIG. 3 is a plot of the active pharmaceutical ingredient amount of several exemplary formulations over a three month time span.
Figure 4:
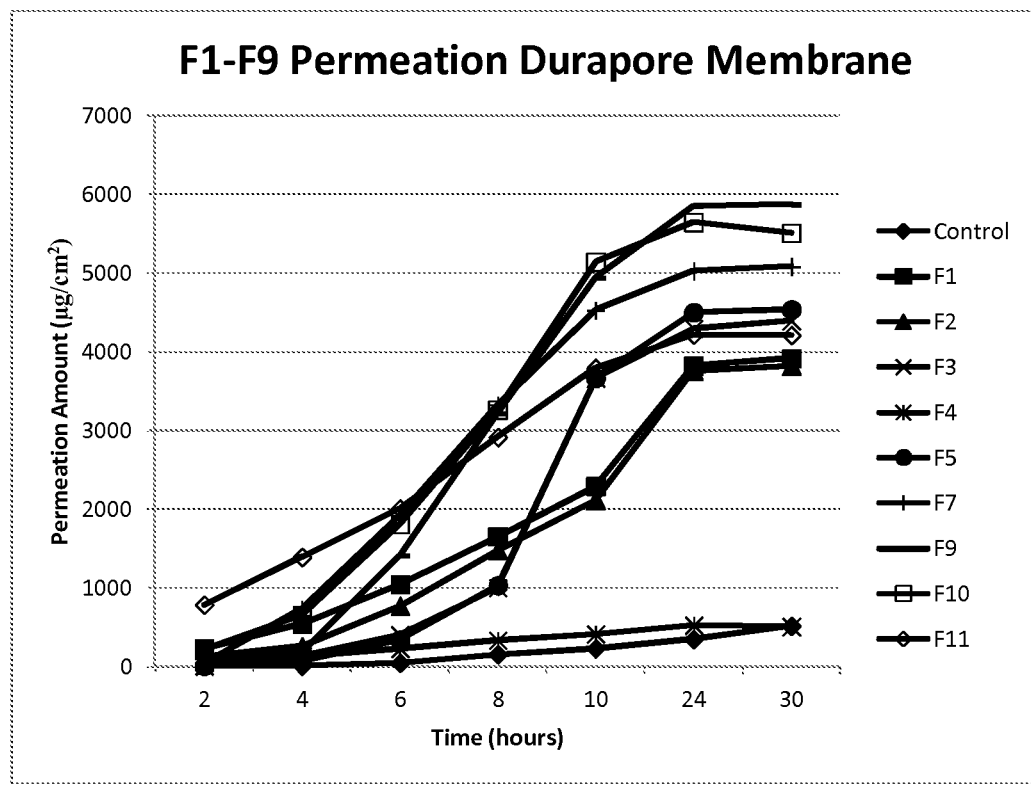
FIG. 4 is a plot of the permeation of the active ingredient of several of the exemplary formulations through a Durapore® membrane.

The API assay results for each of the formulations is plotted and shown in FIG. 3. Formulations F1, F2, F3, F4, F5, F8, F10 and F11 showed reduced active degradation over the control formulation following 12 weeks of storage. The reduction in degradation of API over the control formulation may become more pronounced in certain test formulations at extended periods of time, e.g. 6 months, 12 months, 24 months.

Example 6

Delivery through Durapore® Membrane of the Formulations of Example 1

Select formulations and the control described in Example 1 were tested for penetration through the Durapore® membrane. A total of 10 formulations were tested. The Durapore® membrane is a hydrophilic polyvinylidene fluoride membrane with a 0.45 μm pore size. The amount of halobetasol propionate that diffused through the Durapore membrane into the receptor fluid was quantified at hours 2, 4, 6, 8, 10, 24, and 30. The results are included in Table 6A.

TABLE 5

| | | | | | Active Pharmaceutical Ingredient (API) (%) | | | | | | | |
|---|---|---|---|---|---|---|---|---|---|---|---|---|
| Week | C1 Control | F1 | F2 | F3 | F4 | F5 | F6 | F7 | F8 | F9 | F10 | F11 |
| 0 | 102.5 | 102.3 | 102.2 | 102.4 | 102.4 | 101.5 | 101.6 | 101.1 | 102.2 | 101.9 | 101.3 | 101.3 |
| 4 | 99.8 | 100.3 | 100.5 | 100.5 | 100.0 | 100.4 | 100 | 99.1 | 100.1 | 100.3 | 100.1 | 98.9 |
| 8 | 102.6 | 102.2 | 101.4 | 102.1 | 102.0 | 101.8 | 101.9 | 100.5 | 102.3 | 102.2 | 101.9 | 101.7 |
| 12 | 101.0 | 101.5 | 101.1 | 101.3 | 101.1 | 101.2 | 98.8 | 98.0 | 101.0 | 99.3 | 100.5 | 100.3 |
| Total Change* | 1.5 | 0.8 | 1.1 | 1.1 | 1.3 | 0.3 | 2.8 | 3.1 | 1.2 | 2.6 | 0.8 | 1 |

*Calculated as change in API between 0-week timepoint and 12-week timepoint.

TABLE 6A

Diffusion of Halobetasol Propionate through Durapore ® Membrane

| Time (hours) | Control | F1 | F2 | F3 | F4 | F5 | F7 | F9 | F10 | F11 |
|---|---|---|---|---|---|---|---|---|---|---|
| 2 | 16.65 | 228.81 | 128.1 | 10.56 | 57.22 | 15.26 | 46.74 | 58.38 | 218.01 | 786.64 |
| 4 | 15.39 | 544.73 | 261.09 | 135.37 | 131.91 | 72.88 | 735.87 | 183.14 | 655.06 | 1392.31 |
| 6 | 50.64 | 1048.57 | 774.24 | 404.35 | 229.19 | 343.75 | 1923.86 | 1414.31 | 1813.25 | 2009.5 |
| 8 | 156.67 | 1654.93 | 1475.49 | 1001.02 | 336.98 | 1034.7 | 3325.24 | 3219.19 | 3265.42 | 2917.09 |
| 10 | 231.19 | 2296.47 | 2116.4 | 3664.81 | 415.6 | 3668.02 | 4528.02 | 4941.46 | 5142.33 | 3797.72 |
| 24 | 348.98 | 3828.18 | 3757.6 | 4295.24 | 526.23 | 4501.34 | 5028.3 | 5853.46 | 5648.37 | 4216.92 |
| 30 | 519.22 | 3916.49 | 3823.75 | 4395.79 | 511.34 | 4536.92 | 5085.83 | 5874.12 | 5509.76 | 4211.38 |
| Total | 1338.73 | 13518.18 | 12336.67 | 13907.13 | 2208.46 | 14172.86 | 20673.85 | 21544.07 | 22252.19 | 19331.57 |

The total amount of halobetosal propionate delievered during the treatment period and percent increase compared to the control is included in Table 6B. The presence of the MMPE™s in the test formulations improved penetration of the halobetasol propionate by as much as 1,600%.

TABLE 6B

Percent Increase of Total Diffusion During the Testing Period

| | Control | F1 | F2 | F3 | F4 | F5 | F7 | F9 | F10 | F11 |
|---|---|---|---|---|---|---|---|---|---|---|
| Amount | 1338.73 | 13518.18 | 12336.67 | 13907.13 | 2208.46 | 14172.86 | 20673.85 | 21544.07 | 22252.19 | 19331.57 |
| % Increase | | 1009.78 | 921.52 | 1038.83 | 164.97 | 1058.68 | 1544.29 | 1609.29 | 1662.19 | 1444.02 |

Examples 7-14

Materials and Methods for Examples 7-14

A number of formulations (described in Examples 7-14 below) containing diclofenac sodium (a non-steroidal anti-inflammatory drug or NSAID) were tested for permeation through porcine skin using the Franz diffusion cells [as generally described in Franz T J: Percutaneous absorption. On the relevance of in vitro data. J. Invest Dermatol 1975; 64:190-195].

More specifically, Franz cells with a 5 ml receptor well volume were used in conjunction with full-thickness porcine skin harvested at Perry Scientific (San Diego, Calif.). The porcine skin was shaved free of hair, washed with water and subcutaneous fat was removed. The donor well had an area of ~0.5 cm². Receptor wells were filled with isotonic phosphate buffered saline (PBS) doped with 0.01% sodium azide. The flanges of the Franz cell were coated with vacuum grease to ensure a complete seal and were clamped together with uniform pressure using a pinch clamp (SS #18 VWR 80073-350).

After the Franz cells were assembled, the porcine skin was allowed to pre-hydrate for 45 minutes with isotonic PBS. Isotonic PBS was then removed and 200 ml of the formulation was applied to the donor well. Receptor wells of the Franz cells were maintained at 37° C. (temperature on the surface of the skin is ~30° C.) in a stirring block with continual agitation via a stir bar.

The flux rates were calculated by assuming a radius of 0.4 cm in the donor well (i.e., an area of 0.503 cm²). The HPLC calibration curve for diclofenac was determined to have a slope of 115.6 AUC/(μg diclofenac/ml).

Samples were drawn from the receptor wells at t=24 hours and t=46 hours for all formulations. Franz diffusion cell measurements were made in five-fold replicates for each formulation.

The concentration of diclofenac in the samples was measured using HPLC analysis. Specifically, HPLC was carried out with C18 column and using acetonitrile and water as the mobile phase. Flux rates were calculated using standard equations based on the total transference of diclofenac across the skin after 46 hours. Thus, flux rates, F, were computed according to $$F = \frac{D*V}{t*A},$$

wherein: D is the concentration of the drug in the receptor well after incubation time t, V is the volume of the receptor well and A is the surface area of skin.

Individual penetration enhancers in the Examples discussed below were obtained from the following sources:
- glyceryl oleate (glycerol monooleate) from TCI (VWR), product code TCG0082
- isopropyl myristate from Sigma product code M0757
- methyl laurate from Chem Service product code CSO426
- N-lauroyl sarcosine from Sigma product code L5000
- oleic acid (octadecenoic acid) from Mallinckroft (VWR) product code MK274404
- sodium lauryl sulfoacetate from Stepan (65-72%) product code Lathanol LAL
- sodium octyl sulfate from Alfa Aesar (VWR) product code AA43750-06

The base composition used for each formulation of a carrier composition comprised isotonic PBS, ethanol, propylene glycol and propylene glycol 300 in a volume ratio of 2:2:1:1. The base formulation further comprised diclofenac sodium in a concentration of 1.5 wt % per unit volume of the base composition. In the Examples below, various combinations of the MMPE™s detailed below were added to the base composition.

Example 7

NLS and IM

In this Example, N-lauroyl sarcosine (NLS) and isopropyl myristate (IM) were added to the base formulation. The details of each formulation and the results of the Franz diffusion cell experiments are set out in Table 7 below.

TABLE 7

| Formulation | [NLS + IM] (wt %/vol) | Weight Ratio of NLS:IM | Flux (µg/hr/cm$^2$) |
|---|---|---|---|
| A | 3.0 | 1:1 | 3.80 |
| B | 5.0 | 1:1 | 0.53 |
| C | 5.0 | 1:0 | 0.26 |
| D | 5.0 | 0:1 | 0.02 |

With reference to Table 7, it can be seen that Formulation B (containing a mixture of NLS and IM each at a concentration 2.5% wt/vol) was more effective at enhancing diclofenac sodium flux rates through the skin when compared to either of Formulation C (containing 5% wt/vol NLS and no IM) or Formulation D (containing 5% wt/vol IM and no NLS). Further and surprisingly, Formulation A (containing a mixture of NLS and IM each at a concentration of 1.5% wt/vol) was approximately seven times more effective at enhancing the flux rate of the diclofenac sodium when compared to Formulation B.

Example 8

In this Example, N-lauroyl sarcosine (NLS) and oleic acid (OA) were added to the base formulation. The details of each formulation and the results of the Franz diffusion cell experiments are set out in Table 8.

TABLE 8

| Formulation | [NLS + OA] (wt %/vol) | Weight Ratio of NLS:OA | Flux (µg/hr/cm$^2$) |
|---|---|---|---|
| E | 3.0 | 1:1 | 3.29 |
| F | 5.0 | 1:0 | 0.26 |
| G | 5.0 | 0:1 | 2.70 |

With reference to Table 8, it can be seen that Formulation E (containing a mixture of NLS and OA each at a concentration 1.5% wt/vol) was more effective at enhancing diclofenac sodium flux rate through the skin when compared to either of Formulation F (containing 5% wt/vol NLS and no OA) or Formulation G (containing 5% wt/vol OA and no NLS).

It is notable that the flux rate of the NSAID in Formulation E was higher than that achieved by either of Formulation F or Formulation G in spite of the fact that the total concentration of the molecular penetration enhancers in Formulation E was lower than that in Formulation F and Formulation G.

Example 9

In this Example, sodium octyl sulfate (SOS) and oleic acid (OA) were added to the base formulation. The details of each formulation and the results of the Franz diffusion cell experiments are set out in Table 9.

TABLE 9

| Formulation | [SOS + OA] (wt %/vol) | Weight Ratio of | Flux (µg/hr/cm$^2$) |
|---|---|---|---|
| H | 5.0 | 3:7 | 4.73 |
| I | 5.0 | 1:0 | 2.70 |
| J | 5.0 | 0:1 | 0.02 |

With reference to Table 9, it can be seen that Formulation H (containing a mixture of SOS and OA each at a concentration 1.5% wt/vol and 3.5% wt/vol, respectively) was more effective at enhancing diclofenac sodium flux rate through the skin when compared to either of Formulation I (containing 5% wt/vol OA and no SOS) or Formulation J (containing 5% wt/vol SOS and no OA).

Example 10

In this Example, glyceryl oleate (GO) and sodium octyl sulfate (SOS) were added to the base formulation. The details of each formulation and the results of the Franz diffusion cell experiments are set out in Table 10.

TABLE 10

| Formulation | [GO + SOS] (wt %/vol) | Weight Ratio of | Flux (µgl/cm$^2$) |
|---|---|---|---|
| K | 3.0 | 1:1 | 0.30 |
| L | 5.0 | 1:0 | 0.34 |
| M | 5.0 | 0:1 | 0.02 |

With reference to Table 10, it can be seen that Formulation K (containing a mixture of GO and SOS each at a concentration 1.5% wt/vol) was approximately as effective at enhancing diclofenac sodium flux rate through the skin as Formulation L (containing 5% wt/vol GO and no SOS) and was substantially improved over that of Formulation M (containing 5% wt/vol SOS and no GO).

Example 11

In this Example, glyceryl oleate (GO) and methyl laurate (ML) were added to the base formulation. The details of each formulation and the results of the Franz diffusion cell experiments are set out in Table 11.

TABLE 11

| Formulation | [GO + ML] (wt %/vol) | Weight Ratio of | Flux (µg/hr/cm$^2$) |
|---|---|---|---|
| N | 5.0 | 1:1 | 0.54 |
| O | 5.0 | 1:0 | 0.34 |
| P | 5.0 | 0:1 | 0.32 |

With reference to Table 11, it can be seen that Formulation N (containing a mixture of GO and ML each at a concentration 2.5% wt/vol) was more effective at enhancing diclofenac sodium flux rate through the skin when compared to either of Formulation O (containing 5% wt/vol GO and no ML) or Formulation P (containing 5% wt/vol ML and no GO).

Example 12

In this Example, sodium lauryl sulfoacetate (SLSA) and methyl laurate (ML) were added to the base formulation.

The details of each formulation and the results of the Franz diffusion cell experiments are set out in Table 12.

TABLE 12

| Formu-lation | [SLSA + ML] (wt %/vol) | Weight Ratio of SLSA:ML | Flux (μg/hr/cm$^2$) |
|---|---|---|---|
| Q | 5.0 | 3:7 | 0.52 |
| R | 5.0 | 1:0 | 0.22 |
| S | 5.0 | 0:1 | 0.32 |

With reference to Table 12, it can be seen that Formulation Q (containing a mixture of SLSA and ML each at a concentration 2.5% wt/vol) was more effective at enhancing diclofenac sodium flux rate through the skin when compared to either of Formulation R (containing 5% wt/vol SLSA and no ML) or Formulation S (containing 5% wt/vol ML and no SLSA).

Example 13

In this Example, sodium lauryl sulfoacetate (SLSA) and isopropyl myristate (IM) were added to the base formulation. The details of each formulation and the results of the Franz diffusion cell experiments are set out in Table 13.

TABLE 13

| Formu-lation | [SLSA + IM] (wt %/vol) | Weight Ratio of SLSA:IM | Flux (μg/hr/cm$^2$) |
|---|---|---|---|
| T | 5.0 | 1:1 | 0.52 |
| U | 5.0 | 1:0 | 0.22 |
| V | 5.0 | 0:1 | 0.02 |

With reference to Table 13, it can be seen that Formulation T (containing a mixture of SLSA and IM each at a concentration 2.5% wt/vol) was more effective at enhancing diclofenac sodium flux rate through the skin when compared to either of Formulation U (containing 5% wt/vol SLSA and no IM) or Formulation V (containing 5% wt/vol IM and no SLSA).

Materials and Methods for Example 14

Using methodology similar to that described in Examples 8-13, a number of formulations containing other active agents (as described in greater detail below) were tested for permeation through porcine skin using Franz diffusion cells.

Franz Cell Guidelines:

Skin Preparation: Porcine skin was sourced from Lampire Biological Laboratories (Pipersville, Pa.). The skin was then dermatomed in house to a set thickness.

Diffusion Cell Assembly: Diffusion cells were assembled using dermatomed porcine skin as the substrate. Cell assembly was carried out by clamping the skin between a donor well (the flange was coated with a thin coating of vacuum grease to ensure a proper seal) and a receptor well. The wells were clamped together and held in place using a spring clamp. The receptor wells had a volume of 3.3 ml and the clamped skin had an available surface area of ~0.55 cm$^2$ for the diffusion study. Once the cell was assembled, the receptor well was filled with PBS containing 0.01 wt % NaN$_3$ (to help prevent skin degradation). Care was taken to ensure all bubbles are removed from the receptor solution. The skin was allowed to pre-hydrate for 20 minutes before the formulations were applied to the skin.

Diffusion Cell Testing: After the skin was prehydrated, 40 μl of the test formulation was applied to the skin with a positive displacement pipettor and the applied dose then rubbed gently across the skin with a glass stir rod. Once the formulation was applied, a stir bar was added to the receptor well. The receptor well was maintained at 32° C. and continuously agitated throughout the experiment. Sample aliquots were drawn from the receptor well at varying time points and replaced with fresh PBS buffer. Sample aliquots were filtered and analyzed for concentration of the active using HPLC analysis. Measurements for each formulation were carried out in six-fold replicates.

The individual penetration enhancers used in Example 7 are provided in the following table along with their abbreviation (Abbr) and Chemical Abstract Service (CAS) registry number:

| Abbr. | Chemical | CAS No. |
|---|---|---|
| IM | Isopropyl Myristate | 110-27-0 |
| SLSA | Sodium Lauryl Sulfoacetate | 1847-58-1 |
| OA | Oleic Acid | 112-801-1 |
| ML | Methyl Laurate | 111-82-0 |
| GO | Glyceryl Monooleate | 31566-31-1 |
| NLS | N-lauroyl Sarcosine | 97-78-9 |

Numerous formulations were prepared with the MMPE™s used in conjunction with varying active agents. MMPE™s tested were SLSA/IM, SLSA/ML, IM/NLS, GO/ML, and NLS/OA in a hydroalcoholic solution. These MMPE™s were tested with the active agents ibuprofen, buprorion HCl, ketoprofen, and testosterone. Tables 14A-14J list the MMPE™s that showed a significant increase in flux when compared to flux from the analogous formulations containing only one of the MMPE™s.

TABLE 14A

| Formu-lation | Ibuprofen (wt/wt %) | SLSA (wt/wt %) | IM (wt %/wt %) | Flux (μg/hr/cm$^2$) |
|---|---|---|---|---|
| W | 5 | 3 |  | 42.1 |
| X | 5 |  | 3 | 28.5 |
| Y | 5 | 1.5 | 1.5 | 66.5 |

TABLE 14B

| Formu-lation | Ibuprofen (wt %/wt %) | SLSA (wt %/wt %) | ML (wt %/wt %) | Flux (μg/hr/cm$^2$) |
|---|---|---|---|---|
| Z | 5 | 3 |  | 42.1 |
| AA | 5 |  | 3 | 25.2 |
| BB | 5 | 1.5 | 1.5 | 53.9 |

TABLE 14C

| Formu-lation | Ibuprofen (wt %/wt %) | IM (wt %/wt %) | NLS (wt %/wt %) | Flux (μg/hr/cm$^2$) |
|---|---|---|---|---|
| CC | 5 | 3 |  | 28.5 |
| DD | 5 |  | 3 | 10.0 |
| EE | 5 | 1.5 | 1.5 | 31.0 |

TABLE 14D

| Formu-lation | Ibuprofen (wt %/wt %) | GO (wt %/wt %) | ML (wt %/wt %) | Flux (μg/hr/cm$^2$) |
|---|---|---|---|---|
| FF | 5 | 3 |  | 14.4 |
| GG | 5 |  | 3 | 25.2 |
| HH | 5 | 1.5 | 1.5 | 53.6 |

TABLE 14E

| Formulation | Bupropion HCl (wt %/wt %) | NLS (wt %/wt %) | OA (wt %/wt %) | Flux (μg/hr/cm²) |
|---|---|---|---|---|
| II | 5 | 3 | | 14.3 |
| JJ | 5 | | 3 | 9.1 |
| KK | 5 | 1.5 | 1.5 | 18.8 |

TABLE 14F

| Formulation | Bupropion HCl (wt %/wt %) | SLSA (wt %/wt %) | IM (wt %/wt %) | Flux (μg/hr/cm²) |
|---|---|---|---|---|
| LL | 5 | 3 | | 34.3 |
| MM | 5 | | 3 | 14.5 |
| NN | 5 | 1.5 | 1.5 | 45.6 |

TABLE 14G

| Formulation | Bupropion HCl (wt %/wt %) | SLSA (wt %/wt %) | ML (wt %/wt %) | Flux (μg/hr/cm²) |
|---|---|---|---|---|
| OO | 5 | 3 | | 34.3 |
| PP | 5 | | 3 | 14.8 |
| QQ | 5 | 1.5 | 1.5 | 51.3 |

TABLE 14H

| Formulation | Bupropion HCl (wt %/wt %) | IM (wt %/wt %) | NLS (wt %/wt %) | Flux (μg/hr/cm²) |
|---|---|---|---|---|
| RR | 5 | 3 | | 14.5 |
| SS | 5 | | 3 | 14.3 |
| TT | 5 | 1.5 | 1.5 | 55.9 |

TABLE 14I

| Formulation | Ketoprofen (wt %/wt %) | NLS (wt %/wt %) | OA (wt %/wt %) | Flux (μg/hr/cm²) |
|---|---|---|---|---|
| UU | 5 | 3 | | 14.3 |
| VV | 5 | | 3 | 9.1 |
| WW | 5 | 1.5 | 1.5 | 18.8 |

TABLE 14J

| Formulation | Testosterone (wt %/wt %) | SLSA (wt %/wt %) | IM (wt %/wt %) | Flux (μg/hr/cm²) |
|---|---|---|---|---|
| XX | 5 | 3 | | 14.3 |
| YY | 5 | | 3 | 9.1 |
| ZZ | 5 | 1.5 | 1.5 | 18.8 |

What is claimed is:

1. A topical formulation, comprising:
   at least one corticosteroid,
   a first compound, and
   a second compound,
   wherein the first compound and the second compound are different, and each is selected from the group consisting of N-lauroyl sarcosine, sodium octyl sulfate, methyl laurate, isopropyl myristate, oleic acid, glyceryl oleate, and sodium lauryl sulfoacetate.

2. The topical formulation of claim 1, wherein the first compound and the second compound are each selected from the group consisting of methyl laurate, isopropyl myristate, oleic acid, glyceryl oleate, and sodium lauryl sulfoacetate.

3. The topical formulation of claim 1, wherein the at least one corticosteroid is a pharmaceutically acceptable salt of a corticosteroid.

4. The topical formulation of claim 1, wherein the at least one corticosteroid is a pharmaceutically acceptable base of a corticosteroid.

5. The topical formulation of claim 1, wherein the at least one corticosteroid is selected from the group consisting of clobetasol, halobetasol, betamethasone, triamcinolone acetonide, and combinations thereof.

6. The topical formulation of claim 1, wherein the at least one corticosteroid is halobetasol propionate.

7. The topical formulation of claim 6, wherein the halobetasol propionate is present at about 0.01 wt % to about 20 wt % of the formulation.

8. The topical formulation of claim 7, wherein the halobetasol propionate is present at about 0.05 wt % of the formulation.

9. The topical formulation of claim 1, wherein the first compound comprises methyl laurate and the second compound comprises isopropyl myristate.

10. The topical formulation of claim 1, wherein the first compound comprises methyl laurate and the second compound comprises oleic acid.

11. The topical formulation of claim 1, wherein the first compound comprises methyl laurate and the second compound comprises glyceryl oleate.

12. The topical formulation of claim 1, wherein the first compound comprises methyl laurate and the second compound comprises sodium lauryl sulfoacetate.

13. The topical formulation of claim 1, wherein the first compound comprises isopropyl myristate and the second compound comprises oleic acid.

14. The topical formulation of claim 1, wherein the first compound comprises isopropyl myristate and the second compound comprises glyceryl oleate.

15. The topical formulation of claim 1, wherein the first compound comprises isopropyl myristate and the second compound comprises sodium lauryl sulfoacetate.

16. The topical formulation of claim 1, wherein the first compound comprises oleic acid and the second compound comprises glyceryl oleate.

17. The topical formulation of claim 1, wherein the first compound comprises oleic acid and the second compound comprises sodium lauryl sulfoacetate.

18. The topical formulation of claim 1, wherein the first compound comprises glyceryl oleate and the second compound comprises sodium lauryl sulfoacetate.

19. The topical formulation of claim 1, further comprising one or more biologically acceptable excipients.

20. The topical formulation of claim 19, further comprising polyoxyl 35 castor oil.

21. The topical formulation of claim 1, wherein the formulation further comprises water.

22. The topical formulation of claim 1, wherein the total concentration of the first compound and the second compound is in the range from about 1 wt % to about 5 wt %, per unit volume of the formulation.

23. The topical formulation of claim 1, wherein the total concentration of the first compound and the second compound is up to about 10 wt %, per unit volume of the formulation.

24. The topical formulation of claim 1, wherein the weight ratio of the first compound to the second compound is in the range from about 1:9 to about 9:1.

25. The topical formulation of claim 1, wherein the weight ratio of the first compound to the second compound is in the range of from about 1:3 to about 3:1.

26. The topical formulation of claim 1, wherein the weight ratio of the first compound to the second compound is in the range of from about 1:2 to about 2:1.

27. The topical formulation of claim 1, wherein the weight ratio of the first compound to the second compound is about 1:1.

28. The topical formulation of claim 1, wherein the topical formulation provides for improved flux of the drug as compared to a comparative formulation devoid of the first compound and the second compound and replaced with an equivalent wt % of water.

29. The topical formulation of claim 1, wherein the topical formulation has improved chemical and/or physical stability as compared to a comparative formulation devoid of the first compound and the second compound and replaced with an equivalent wt % of water.

30. A method of treating a skin condition, comprising:
applying a topical formulation of a corticosteroid to a skin surface of a subject at a site of the skin condition, said formulation comprising:
at least one corticosteroid,
a first compound, and
a second compound, wherein the first compound and second compound are different and each is selected from the group consisting of N-lauroyl sarcosine, sodium octyl sulfate, methyl laurate, isopropyl myristate, oleic acid, glyceryl oleate, and sodium lauryl sulfoacetate.

31. The method of claim 30, wherein the at least one corticosteroid is selected from the group consisting of a clobetasol, halobetasol, betamethasone, triamcinolone acetonide, and combinations thereof.

32. The method of claim 30, wherein the at least one corticosteroid is halobetasol propionate.

33. The method of claim 30, wherein the first compound comprises methyl laurate and the second compound comprises isopropyl myristate.

34. The method of claim 30, wherein the first compound comprises methyl laurate and the second compound comprises oleic acid.

35. The method of claim 30, wherein the first compound comprises methyl laurate and the second compound comprises glyceryl oleate.

36. The method of claim 30, wherein the first compound comprises methyl laurate and the second compound comprises sodium lauryl sulfoacetate.

37. The method of claim 30, wherein the first compound comprises isopropyl myristate and the second compound comprises oleic acid.

38. The method of claim 30, wherein the first compound comprises isopropyl myristate and the second compound comprises glyceryl oleate.

39. The method of claim 30, wherein the first compound comprises isopropyl myristate and the second compound comprises sodium lauryl sulfoacetate.

40. The method of claim 30, wherein the first compound comprises oleic acid and the second compound comprises glyceryl oleate.

41. The method of claim 30, wherein the first compound comprises oleic acid and the second compound comprises sodium lauryl sulfoacetate.

42. The method of claim 30, wherein the first compound comprises glyceryl oleate and the second compound comprises sodium lauryl sulfoacetate.

43. The method of claim 30, wherein the formulation further comprises polyoxyl 35 castor oil.

44. The method of claim 30, wherein the skin condition is caused by eczema, dermatitis, allergy, or a skin rash.

45. The method of claim 30, wherein the skin condition is caused by psoriasis.

46. The method of claim 30, wherein the skin condition is plaque psoriasis.

* * * * *